(12) United States Patent
Dolly et al.

(10) Patent No.: US 7,628,992 B1
(45) Date of Patent: Dec. 8, 2009

(54) MODIFICATION OF CLOSTRIDIAL TOXINS FOR USE AS TRANSPORT PROTEINS

(75) Inventors: James Oliver Dolly, Portmarnock (IE); Larry Allen Wheeler, Irvine, CA (US); Kei Roger Aoki, Coto de Caza, CA (US); Michael Elwood Garst, Newport Beach, CA (US)

(73) Assignee: Invent DCU Limited, Glasnevin, Dublin ( * ) Notice: Subject to any disclaimer, the term of this patent is extended or adjusted under 35 U.S.C. 154(b) by 761 days.

(21) Appl. No.: 09/676,053

(22) Filed: Sep. 28, 2000

Related U.S. Application Data

(62) Division of application No. 08/750,101, filed on May 1, 1997, now Pat. No. 6,203,794.

(30) Foreign Application Priority Data

| May 31, 1994 | (GB) | ................................. 9410871.1 |
| May 31, 1994 | (GB) | ................................. 9410871.9 |

(51) Int. Cl.
- *A61K 39/395* (2006.01)
- *A61K 39/02* (2006.01)
- *A61K 38/00* (2006.01)
- *C07K 14/00* (2006.01)

(52) U.S. Cl. .............................. 424/197.11; 424/184.1; 424/234.1; 424/235.1; 424/236.1; 424/239.1; 424/247.1; 424/183.1; 424/178.1; 424/179.1; 424/164.1; 424/167.1; 424/832; 530/350; 530/300

(58) Field of Classification Search ............... 424/184.1, 424/234.1, 235.1, 236.1, 239.1, 247.1, 183.1, 424/164.1, 179.1, 178.1, 197.11, 167.1, 832; 530/350, 300
See application file for complete search history.

(56) References Cited

U.S. PATENT DOCUMENTS

| 4,594,336 A | 6/1986 | Bizzini |
| 4,713,240 A | 12/1987 | Wilkins et al. |
| 5,204,097 A | 4/1993 | Amon et al. |
| 5,437,291 A | 8/1995 | Pasricha et al. |
| 5,443,976 A | 8/1995 | Carroll |
| 5,512,547 A | 4/1996 | Johnson et al. |
| 5,562,907 A | 10/1996 | Amon |
| 5,585,100 A | 12/1996 | Mond et al. |
| 5,599,539 A | 2/1997 | Carroll et al. |
| 5,601,823 A | 2/1997 | Williams et al. |
| 5,650,280 A | 7/1997 | Stuart et al. |
| 5,674,205 A | 10/1997 | Pasricha et al. |
| 5,693,476 A | 12/1997 | Scheller |
| 5,719,267 A | 2/1998 | Carroll et al. |
| 5,721,215 A | 2/1998 | Aoki et al. |
| 5,736,139 A | 4/1998 | Kink et al. |
| 5,762,934 A | 6/1998 | Williams et al. |
| 5,814,477 A | 9/1998 | Williams et al. |
| 5,919,665 A | 7/1999 | Williams |
| 5,955,368 A | 9/1999 | Johnson et al. |
| 5,965,699 A | 10/1999 | Schmidt et al. |

FOREIGN PATENT DOCUMENTS

| EP | 0254905 | 3/1988 |
| WO | 9400487 | 1/1994 |
| WO | 9421300 | 9/1994 |
| WO | 00/33880 | 6/2000 |

OTHER PUBLICATIONS

De Paiva et al., *J. Biol. Chem*, 268:20838 (1993).
Weller et al., *Eur. J. Biochem*. 182:649(1989).
Bizzini et al, Journal of Neurochemistry, 1977, vol. 28, pp. 529-542, "An Antigenic Polypeptide Fragment Isolated From Tetanus Toxin: Chemical Characterization, Binding To Gangliosides and Retrograde Axonal Transport in Various Neuron Systems".
Dertzbaugh et al, Vaccine 14/6: 1538-44, 1996.
Thompson et al, Eur. J. Biochem. 189:73-81, 1990.
Kozaki et al, Microbiol, Immunol. 39/ 10: 767-774, 1995.
Pellizzari et al, Phil. Trans. R. Soc. Lond. 354: 259-268, 1999.

*Primary Examiner*—Robert A Zeman
(74) *Attorney, Agent, or Firm*—Stout, UXA, Buyan & Mullins, LLP; Carlos A. Fisher

(57) ABSTRACT

A chemical conjugate for treating a nerve cell related disorder is provided. This conjugate includes an active or inactive Clostridial toxin having specificity for a target nerve cell. The toxin is conjugated to a drug or other bioactive molecule without affecting the toxin's ability to enter the target nerve cell.

8 Claims, 9 Drawing Sheets

FIG. 6A.

BoNT/A cleavage site (Gln197/Arg198)

1    195    206    SNAP-25

Peptide antigen
CANQRATKMLGSG

MODIFICATION OF CLOSTRIDIAL TOXINS FOR USE AS TRANSPORT PROTEINS

This application is a divisional of Ser. No. 08/750,101, filed May 1, 1997, now U.S. Pat. No. 6,203,794 which was a Section 371 of international patent application PCT/GB95/01253, filed May 31, 1995, which claimed priority to British patent applications GB 9410871.9 and GB10871.1, both filed May 31, 1994, collectively incorporated by reference herein.

FIELD OF THE INVENTION

The present invention relates generally to the field of receptor-targeted biochemical delivery systems. More specifically, this invention relates to the use of modified polypeptide toxins as vehicles for delivering chemical compounds to cells bearing toxin receptors.

BACKGROUND OF THE INVENTION

Tetanus toxin (TeTx) and botulinum toxin (BoNT) are potent neurotoxins that induce paralysis by mechanisms that involve the inhibition of neurotransmitter release. These Clostridial neurotoxins are initially produced as single-chain proteins of ~150 kDa. Proteolytic cleavage then generates an active dichain molecule having a ~100 kDa heavy (H) and a ~50 kDa light (L) chain that are linked by a single interchain disulfide bond. The H chain contains domains which contribute to the binding of the toxin to neuronal cell surface receptors and which facilitate translocation of the L chain into cells. The L chain is responsible for blocking neurotransmitter release.

The mechanisms of toxin action have recently been clarified. The TeTx-L chain is a zinc-dependent protease specific for the vesicle-associated protein called synaptobrevin or vesicle-associated membrane protein (VAMP). The cleavage of VAMP by the TeTx-L chain inhibits neurotransmitter release by preventing the docking/fusion of transmitter-containing vesicles and the presynaptic membrane.

While a single isoform of TeTx is produced by *Clostridium tetani*, seven serologically distinct isoforms of BoNT are produced by *Clostridia botulinum*. These seven botulinum toxin species are designated as BoNT/A-G. Like tetanus toxin, the botulinum type B neurotoxin is a zinc-dependent protease. In *EMBO J.* 12:4821 (1993), Blasi et al. proposed that the botulinum neurotoxin serotypes have evolved distinct substrate specificities while retaining a common protease activity. Botulinum neurotoxins B, D, F and G also cleave VAMP or a closely related isoform. In contrast, BoNT/A and BoNT/E cleave a synaptosome associated protein of molecular weight 25 kDa (SNAP-25). Finally, BoNT/C has been shown to cleave syntaxin. In addition to these target proteins, TeTx and BoNT/B have been reported to cleave Cellubrevin. Thus, the intraneuronal targets of the Clostridial toxins universally participate in the process of neurotransmitter release.

All of the Clostridial neurotoxins apparently bind different cell surface receptors and proteolyze cellular components that are required for neurotransmitter release. TeTx exerts its effect in the spinal cord and lower brain stem by reducing the activity of inhibitory neurons. The seven isoforms of BoNT all produce a flaccid paralysis. Mechanistically, the botulinum toxins selectively inhibit peripheral cholinergic nerve terminals which are predominantly found at neuromuscular junctions.

Certain zinc-dependent endoproteases contain the conserved amino acid sequence HExxH. In thermolysin, zinc binding is achieved via $His^{142}$ and $His^{146}$ within this motif, together with $Glu^{166}$; the fourth ligand is water. Comparison of tetanus L chain with thermolysin and other zinc endoproteases revealed the presence of the same consensus motif. Conceivably then, $Glu^{234}$ of TeTx-L chain might correspond to the critical $Glu^{145}$ residue in thermolysin.

The role of $Glu^{234}$ within this motif in the L chain of TeTx has been studied using site-directed mutagenesis and an in vitro assay for the proteolysis of cellubrevin. In *Nature* 364: 346 (1993), McMahon et al. demonstrated that cellubrevin was not cleaved when COS cells were cotransfected with mutant L chain ($Glu^{234}$ substituted by Gln) and cellubrevin DNA constructs.

SUMMARY OF THE INVENTION

One aspect of the present invention relates to a chemical conjugate for treating a nerve cell related disorder. This conjugate includes an active or inactive botulinum or tetanus toxin having specificity for a target nerve cell. The toxin is conjugated to a drug or other bioactive molecule without affecting the toxin's ability to enter the target nerve cell. Thus, one aspect of the present invention relates to a chemical conjugate for treating a nerve cell related disorder. The chemical conjugate includes an inactive Clostridial neurotoxin having specificity for a target nerve cell, and a drug or other bioactive molecule attached to the neurotoxin. The neurotoxin retains its ability to enter the target nerve cell. The Clostridial neurotoxin can be any of a variety of such toxins, including tetanus toxin, botulinum toxin A, botulinum toxin B, botulinum toxin C, botulinum toxin D, botulinum toxin E, botulinum toxin F and botulinum toxin G. Inactivation of the Clostridial neurotoxin can be accomplished by an amino acid change in its light chain. Thus, for example, the inactivated Clostridial neurotoxin can be tetanus toxin having a modification of $Glu^{234}$, a botulinum toxin A having a modification at $His^{227}$ and/or $Glu^{224}$, or a botulinum toxin other than botulinum toxin A having a modification at a site corresponding to $His^{227}$ and/or $Glu^{224}$ of botulinum toxin A.

Another aspect of the invention involves the chemical conjugate as described above, for use in the treatment of a neuromuscular dysfunction in a mammal, such as a dysfunction relating to uncontrollable muscle spasms.

The invention also includes the use of the chemical conjugate described above in the preparation of a medicament for treatment of a neuromuscular dysfunction, such as a dysfunction relating to uncontrollable muscle spasms in a mammal.

In a particular aspect of the invention, the drug in the chemical conjugate is an active ingredient for treatment of botulism or tetanus. This aspect of the invention can be used to treat botulism or tetanus in a mammal, and can thus be used in the preparation of a medicament for such treatment.

Another aspect of the invention relates to the use of an inactive Clostridial neurotoxin in the preparation of a medicament for treatment of botulinum toxin poisoning. In this aspect, the inactive Clostridial neurotoxin can be used alone without conjugation to another drug.

An additional aspect of the present relates to the use of chemical conjugate that includes an active clostridial neurotoxin and a drug. Such a conjugate is used in the preparation of a medicament for treatment of focal dystonias, spasticities due to stroke or traumatic brain or spinal cord injury, blepharospasm, strabismus, cerebral palsy or back pain due to muscle spasms.

In still another aspect, the invention relates to a method of treating a neuromuscular dysfunction in a mammal. This method includes the steps of preparing a pharmaceutically active solution which includes a Clostridial neurotoxin linked to a drug, and introducing an effective quantity of the pharmaceutically active solution into a mammal. The neurotoxin can be any of a variety of such toxins, including tetanus toxin, botulinum toxin A, botulinum toxin B, botulinum toxin C, botulinum toxin D, botulinum toxin E, botulinum toxin F and botulinum toxin G. The neurotoxin can be inactivated by an amino acid change in its light chain. In one embodiment, the drug inhibits neurotransmitter release, and in another the drug inhibits the activity of synaptobrevin. In a preferred application of the method, the method is used to treat a neuromuscular dysfunction relating to uncontrollable muscle spasms.

Further aspects of the present invention will be apparent to one having ordinary skill in the art upon reference to the ensuing detailed description.

BRIEF DESCRIPTION OF THE FIGURES

FIG. 1 is a schematic representation of the TeTx and the DNA construct (pMAL-LC) used to express the MBP-L chain fusion proteins.

FIG. 6 shows the recombinant SNAP-25 substrate for BoNT/A and presents graphic results from a cleavage assay developed by Western blotting. (A) Schematic representation of the C-terminal fragment of SNAP-25 encompassing the BoNT/A cleavage site, against which a polyclonal antibody was raised and the peptide antigen (SEQ ID NO: 11). (B). Graph of the numerical values obtained from densitometric scanning of Western blots. Reduced native BoNT/A (•) and recombinant wild-type L-chain (○) effectively cleaved SNAP-25, while the Tyr$^{227}$ mutant was devoid of proteolytic activity (_).

FIG. 7A is before factor X$_a$ cleavage and FIG. 7B is after Factor X$_a$ cleavage. Cells were permeabilized by incubation for 15 minutes with 20 μM digitonin in KGEP buffer (139 mM K$^+$glutamate, 5 mM ethylene glycol-bis[β-aminoethyl ether] N,N,N',N'-tetraacetic acid [EGTA], 2 mM ATP, 2 mM MgCl$_2$, 20 mM piperazine-N,N'-bis-[2-ethanesulfonic acid] [PIPES] pH 6.5) containing the indicated concentration of native BoNT/A (○; Δ) or recombinant L chain fusion protein before (●) or after (▲) cleavage with Factor X$_a$. Following a brief rinse with KGEP, cells were incubated for 15 minutes with KGEP with or without 20 μM free Ca$^{2+}$. An aliquot was then removed from each well and assayed for catecholamine content by a fluorometric method. Catecholamine remaining inside cells was calculated after Tx-100 solubilization, and secretion was calculated as a percentage of the total cell content (=remaining+released). Catecholamine in the Ca$^{2+}$-free buffer was subtracted from that secreted into that containing 20 μM Ca$^{2+}$ to calculate evoked release.

FIG. 9 is a schematic representation of the constructs used to produce MBP-BoNT/A-L chain double mutant ("1") and MBP-TeTx truncated L chain-BoNT/A-L chain double mutant ("2").

DETAILED DESCRIPTION OF THE INVENTION

Figure 1A:
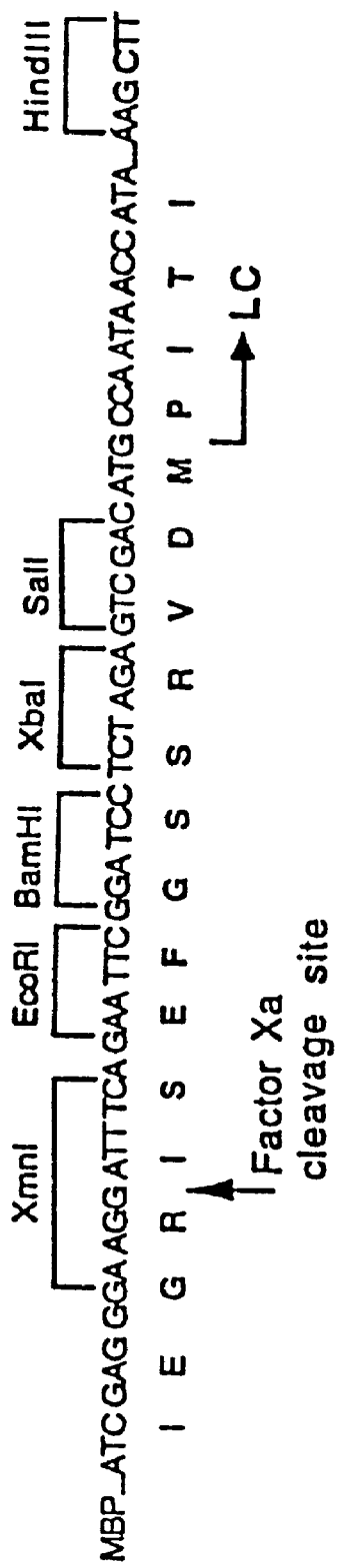
FIG. 1A shows the nucleotide sequence (SEQ ID NO: 14) and amino acid sequence (SEQ ID NO: 10) of the first several residues of the purified recombinant L chain and Ala$^{234}$-L chain determined by N-terminal microsequencing.

The present invention relates to the use of modified Clostridial neurotoxins, in their dichain forms, as transporters for the delivery of linked pharmacologic compounds. Among the compounds that can be linked to the toxin transporters are visualizable agents bearing fluorochromes, and drugs of therapeutic value. Whereas the enzymatic properties of the native toxins could be a disadvantage in such applications, we have discovered a means for overcoming this limitation. The contemplated cell populations that are targeted by the toxin transporters include those which express cognate toxin receptors.

We discovered that an effective drug delivery agent can be prepared by mutating one or more amino acid positions in the L chain of a Clostridial neurotoxin, to inactivate its protease activity, and then attaching a drug to that inactivated neurotoxin. Despite this abolition of enzymatic activity, the mutagenized toxin advantageously retained the ability to bind its cognate cell surface receptor. In addition, we have discovered other unexpected properties of the attenuated Clostridial toxins.

Significantly, we have discovered that both the heavy and L chains of the Clostridial neurotoxins are required for optimal receptor-ligand interaction. In light of this finding, we reasoned that a toxin transporter would advantageously comprise both chains of the dichain molecule. Since the toxic properties associated with the L chain molecule could interfere with the therapeutic effect of a drug that was covalently linked to the transporter, we created an attenuated L chain molecule that was reconstituted with native H chain; the ability of the resultant dichain molecule to bind to the cognate receptor and undergo internalization was retained. We discovered this could be accomplished, with apparently minimal disruption to the folded structure of the L chain protein, by mutation of one or more amino acid positions.

Accordingly, use of the inactivated Clostridial toxin as a vehicle that can be covalently linked to a drug has been explored. Reconstituted toxin, having an inactivated L chain disulfide-bonded to a native H chain, retained the ability to specifically interact with target receptors and become transported to the cytosol, together with the attached molecule. Hence, the inactivated and chemically modified toxin complex can be used as a system for delivering linked chemical compounds to the cytosol of neuronal cells that express cell surface receptors for the toxins.

In the development of the present invention, the gene encoding TeTx-L chain was modified at the 5' end by the addition of a DNA sequence encoding a maltose-binding domain. This domain, therefore, was added to the N-terminal portion of the TeTx-L chain protein. Following expression in *E. coli*, the recombinant fusion protein (called MBP-L chain) was purified by affinity chromatography. Proteolysis by factor $X_a$ allowed separation of the L chain and the MBP domains of the fusion protein. The purified L chain was then combined with purified H chain that had been isolated from *C. tetani*-derived TeTx to generate a dichain. This reconstituted TeTx molecule displayed activities characteristic of the native toxin. Parallel findings have also been made using the recombinant BoNT/A-L chain protein after reassociation with native BoNT/A-H chain protein.

In other experiments, modification of $Glu^{234}$ to Ala in the TeTx-L chain abolished its ability to cleave VAMP or a synthetic substrate that contained the cleavage recognition site for TeTx-L chain. Advantageously, neurotoxicity of the complex formed by the mutant L chain and a wild-type H chain was also abolished, although the modified toxin retained the ability to bind its receptor. In a similar experiment, separate BoNT/A-L chain molecules were modified at either the $His^{227}$ or $Glu^{224}$ or both residues. These modifications in the BoNT/A-L chain caused the loss of proteolytic activity against cellular target substrates.

Since many individuals are immunized against tetanus toxin, it is believed advantageous to further modify the TeTx molecule so that it will be minimally neutralized by circulating antibodies. Modifications to the TeTx molecule that retain its cellular binding and internalization ability, but limit its detection by the immune system are preferred.

By the methods described herein, mutant Clostridial toxins can be synthesized; moreover, they retained the ability to be effectively internalized and transported to the cytosol. These toxins advantageously retain the ability to bind neurons, even in the absence of an associated protease activity. These attenuated toxins are useful in the production of novel systems for the specific delivery of chemical agents to target neurons.

The mutagenized and enzymatically inactive dichain Clostridial toxins described herein can advantageously serve as neuropharmacologic agents for transporting chemical compounds to neuronal cells that express cell surface receptors for the toxins. Bonding of chemical agents to the transporter protein is requisite for practice of the invention. Such chemical agents can be pharmacologic agents, chemotherapeutic agents or visualizable agents that can be detected by light or other form of electromagnetic radiation.

Despite a number of similarities, those of ordinary skill in the art will appreciate that tetanus and botulinum toxins are functionally distinct in at least one important respect. Tetanus toxin is taken up by motor neurons and then transported to the spinal cord where it produces spasticity with convulsions. Thus, Tetx can reach target cells in the spinal cord by a pathway that begins in the muscles and traces back to the spinal cord. Conversely, the various BoNT serotypes all exert localized neurotoxicity at cholinergic nerve terminals, substantially confined to the site of injection.

This difference between the ability of TeTx to transit to the spinal cord and exert toxic activity and the localized activity of BoNT can be exploited in therapeutic protocols employing modified toxin-transporters. In particular, modified toxins based on TeTx are expected to carry linked drugs to the spinal cord along a neural pathway that connects the spinal cord and the injected muscle. Conversely, modified toxins based on one of the botulinum serotypes are expected to remain localized at the site of injection. Hence, a clinician using therapeutic agents based on the modified toxin-transporters of the following invention can selectively deliver drugs to the region of the spinal cord by injecting a TeTx-based therapeutic agent into an appropriate muscle. Alternatively, administration of a BoNT-based therapeutic agent into a muscle is expected to exert activity confined to the motor neurons at the site of injection.

The inactive tetanus toxin transporter can be primarily used to deliver drugs to target tissues for the purpose of controlling spasticity and excess movements in general areas, such as an arm, leg or portion of the body. The drug and transporter can be administered intramuscularly in one or more muscle groups which originate from the spinal cord target. In general, diseases affecting muscles below the neck are ideal targets.

Diseases that are believed to be benefited from such therapies include, but are not limited to, spasmodic torticollis, post stroke or traumatic brain injury induced spasticity, and dystonias of large muscle groups.

The inactive botulinum toxin transporter can be primarily used to deliver drugs that target the peripheral motor nerve terminal. Therefore, diseases which affect limited muscle groups can be most appropriately treated using the BoNT/A based transporter. Transporters based on other botulinum toxin serotypes are also believed effective for this purpose.

Diseases that are believed to benefit from such therapies include, but are not limited to, tardive dyskinesia, spastic colitis, essential tremor, gastric smooth muscles, achalasia (abnormal contractions of the esophagus), localized spasticity, painful muscle spasms localized to back or other muscle groups, temporal mandibular disorders, spasmodic dysphonia (overactive vocal chords), swallowing disorders, tension headaches, spasmodic torticollis, post stroke or traumatic brain injury induced spasticity, dystonias of large muscle groups, cardiovascular smooth muscle (i.e., arteriole), and sphincter smooth muscle found in various organs (gall bladder, urinary bladder, rectum, etc.).

Table 1 outlines potential therapeutics related to the present invention. The entries in this table describe specific drug classes that can be linked to the tetanus toxin or botulinum toxin molecules. As indicated in Table 1, modified tetanus toxin can deliver therapeutic compounds to the spinal cord and other nerve cell sites. Modified botulinum toxins are useful as vehicles for the local delivery of chemical agents.

Although the transporters described herein are primarily inactive dichain tetanus and botulinum toxin type A proteins, the toxins of all other botulinum serotypes (B-G) could similarly be used. The different serotypes of botulinum toxin utilize different presynaptic receptors. Hence, we foresee the use of different toxin serotypes as transporters that can advantageously be used to provide specificity for drug delivery. This would be particularly useful if some tissues selectively expressed one receptor more than any other. Alternatively, two transporters could be used to deliver different therapeutic agents to the same target area of the body. This latter approach would advantageously reduce competition between different toxin ligands at the receptor site.

Additionally, the use of both native and recombinant wild-type Clostridial neurotoxin proteins as transporters for linked chemical compounds is intended to fall within the scope of the present invention. In such applications, the enzymatic activity possessed by the L chain portion of the drug transporter provides an added therapeutic advantage by virtue of its neurotoxic properties. For example, a drug that blocked nerve function could be linked to a wild-type botulinum toxin molecule to provide a compound having a double action. The botulinum toxin would provide its neuronal inhibitory effect, while the drug acted at its target site in the cell.

Examples of neuromuscular maladies that are therapeutic targets using active neurotoxins linked to drug molecules include: focal dystonias, spasticities due to stroke or traumatic brain or spinal cord injury, blepharospasm, strabismus, cerebral palsy and back pain due to muscle spasms.

As indicated below, some of the drugs contemplated for use with the present invention act intracellularly while others act extracellularly. As disclosed herein, the intracellular-acting drugs can be bound to a Clostridial toxin carrier and efficiently internalized. However, extracellular-acting drugs can also be used with the present invention. We have discovered that reduced, alkylated botulinum toxin molecules can bind to the exterior of the cell, but will not be internalized (de Paiva et al., *J. Biol. Chem.* 268:20838 (1993)). Thus, these reduced, alkylated molecules can be linked to extracellular-acting drugs and carried to the target cell's surface. Once bound to the cell surface, enzymes such as esterases can cleave the drug from the toxin carrier thereby releasing the drug in close proximity to the target cell.

A brief description of the various uses of the transporter forms coupled with representative drug classes are summarized below.

TABLE 1

Therapeutic Uses of Clostridial Toxin Transporters

| Transporter Molecule | Tissue Target | Drug Type | Mechanism of Action | Possible Clinical Outcome |
| --- | --- | --- | --- | --- |
| Inactive-intact-tetanus toxin | Spinal cord | GABA agonist | Increase inhibitory neuron activity. | Block spasticity or cause a group of muscles to relax (at cord level), based on muscles injected. |
| Inactive-intact-tetanus toxin | Spinal cord | Neuronal Calcium Channel Agonist | Increase nerve firing of inhibitory neurons of the spinal cord. | Block spasticity or cause a group of muscles to relax (at cord level), based on muscles injected. |
| Inactive-intact-tetanus toxin | Spinal cord | Adenosine agonist | Reduce firing of interneurons at the spinal cord. | Block spasticity or cause a group of muscles to relax (at cord level), based on muscles injected. |
| Inactive-intact-tetanus toxin | Spinal cord | Glutamate antagonist (or other EAA antagonist) | Reduce firing of interneurons at the spinal cord. | Block spasticity or cause a group of muscles to relax (at cord level), based on muscles injected. |
| Inactive-intact-tetanus toxin or Active toxin | Spinal cord | Ricin or other protein synthesis toxins | Selective destruction of motor neurons in spinal cord. | Permanent paralysis. |
| Inactive-intact tetanus toxin | Spinal cord | Captopril and other zinc dependent protease inhibitors, including specially designed inhibitors of enzyme and other activities | Block proteolytic and other actions of the toxin. | Such transporters could be used in the treatment of tetanus when linked appropriately to effective drugs. |

TABLE 1-continued

Therapeutic Uses of Clostridial Toxin Transporters

| Transporter Molecule | Tissue Target | Drug Type | Mechanism of Action | Possible Clinical Outcome |
|---|---|---|---|---|
| Inactive-intact tetanus toxin | Spinal cord | of tetanus toxin Neuronal growth factor (GF) or GF gene and activation promotor | Stimulate growth of neurons. | Treatment of neurodegenerative disease (i.e., ALS, etc.) |
| Inactive-intact tetanus toxin | Spinal cord | Antiviral medication or gene therapy | Block viral replication | Prevent viral related neurodegeneration. |
| Inactive-reduced/ alkylated-botulinum toxin | Peripheral skeletal muscle targeted by injection | Nicotinic antagonist | Binds to ecto-acceptors on motor nerve endings but is not internalized efficiently; the drug could be attached which is released by local acetylcholine esterase. This drug would then block the AChR on the muscle, released from the depot in the synapse. | Prolonged skeletal muscle weakness, reduction of spasticity and/or pain. Duration: hours to several days |
| Inactive-reduced/ alkylated-botulinum toxin or Active intact | Peripheral skeletal muscle targeted by injection | Neuronal calcium channel blocker | Block calcium entry into neuron and thus prevent release of transmitter. Binds to ectoreceptor and released as above. | Prolonged skeletal muscle weakness, reduction of spasticity and/or pain. Duration: hours to several days |
| Inactive-reduced/ alkylated-botulinum toxin | Peripheral skeletal muscle targeted by injection | Acetylcholine esterase inhibitors | Binds to ecto-acceptors on motor nerve endings but is not internalized efficiently. The drug released locally by hydrolysis and blocks acetylcholine esterase. | Enhanced muscle contraction. Could counter the effect of Botox and be used in the treatment of myasthenia gravis. |
| Inactive-intact botulinum toxin or Inactive-reduced/ alkylated | Peripheral skeletal muscle targeted by injection | K+ channel activator | Activate K+ channel and thus reduce Ca++ flow | Muscle weakness |
| Inactive-intact- botulinum toxin | Peripheral skeletal muscle targeted by injection | Vesamicol or analog | Block transport of acetylcholine into the vesicle in the nerve terminal. | Prolonged skeletal muscle weakness, reduction of spasticity and/or pain. Duration: hours to several days |
| Active-intact- botulinum toxin | Peripheral skeletal muscle targeted by injection | Ribozyme or oligonucleotide | Same target mRNA as inactive transporter, above, | Prolonged skeletal muscle weakness or flaccidity, reduction of spasticity and/or pain. Duration: > 3 months |
| Inactive-intact- botulinum toxin | Peripheral skeletal muscle targeted by injection | Captopril and other zinc dependent protease inhibitors, including specially designed inhibitors of enzyme activities or other actions of botulinum toxin serotypes. | Block proteolytic and other actions of the toxins. | Antagonize the effect of a Botox injection, if administered early enough. In particular, such transporters could be used in the treatment of botulism caused by the various toxin serotypes when linked appropriately to effective drugs. |
| Inactive-intact botulinum toxin | Peripheral nerves end ganglion | Antiviral medication or gene therapy | Block viral replication | Prevent viral related neurodegeneration and ulcers/cold sores. |
| Inactive-intact- botulinum toxin | Peripheral skeletal muscle targeted by injection | Ribozyme or oligonucleotide | Prevent synthesis of critical nerve component needed for the neural transmitter exocytosis and/or nerve sprouting/regrowth to reform the synapse at the | Prolonged skeletal muscle weakness or flaccidity. reduction of spasticity and/or pain. Duration: >3 months |

TABLE 1-continued

Therapeutic Uses of Clostridial Toxin Transporters

| Transporter Molecule | Tissue Target | Drug Type | Mechanism of Action | Possible Clinical Outcome |
|---|---|---|---|---|
| | | | neuromuscular junction. (i.e., block nerve muscle communication to establish stable synapse). Alternatively, block synthesis of ion channels. Another target is Choline acetyltransferase. | |

The methods used to covalently couple the inactivated Clostridial toxins and the chemical agents rely on conventional techniques that are familiar to those having ordinary skill in the art. The provision must be met however, that the domain of the compound that corresponds to the inactivated toxin retains the ability to specifically interact with cognate Clostridial toxin receptors on target cells.

Purified botulinum toxin type A has been clinically used as a neurotoxic agent. This compound, which is sold under the trade name BOTOX®, is manufactured by Allergan, Inc. (Irvine, Calif.). This agent is therapeutically used to produce localized chemical denervation muscle paralysis. When chemically denervated in this fashion, the affected muscle atrophies and may develop extrajunctional acetylcholine receptors. It is believed that the affected nerve cells can sprout and reinnervate muscle tissue, thus rendering the paralytic activity of BOTOX® reversible.

Modified Clostridial toxins, produced according to the methods described above, will be stored in lyophilized form in containers under vacuum pressure. Prior to lyophilization, the modified toxins will be combined with pharmaceutically acceptable excipients, including albumins and other appropriate agents as would be appreciated by those of ordinary skill in the art. Further information regarding such pharmaceutical preparations can be found in the "Physicians Desk Reference," published annually by Medical Economics Data of Oradell, N.J. The lyophilized material will be reconstituted with sterile non-preserved saline prior to intramuscular injection. This dissolved material will then be useful in the treatment of a variety of neuromuscular disorders as described above.

Methods of Linking Chemical Compounds to Light Chain Proteins

Whereas we contemplate that many different chemical compounds will be usefully bonded to toxin transporter molecules, a subset of these compounds will be neuropharmacologic agents or drugs. The following description therefore emphasizes methods of joining transporter proteins and drugs. However, those of ordinary skill in the art will appreciate the more generic term, "chemical compound" can reasonably be substituted for the term, "drug."

Many approaches are known for linking chemical compounds to the amino acid chains of proteins. We will use a linker molecule to separate the drug from the L chain peptide. As discussed above, we discovered that 11 amino acids can be attached to the N-terminus of the TeTx-L chain with out substantially affecting its functionality. For this reason, we will use the N-terminal portion of either the botulinum toxin or tetanus toxin L chain as the compound attachment point.

It is known that most drugs have positions that are not sensitive to steric hindrance. In addition, the linkage process should not introduce chirality into the drug molecule. Further, the linker and the drug should be attached through a covalent bond. The distance between the L chain and drug can be adjusted by the insertion of spacer moieties. Preferable spacers have functional groups capable of binding to the linker, drug and L chain and serving to conjugate them.

Preferred Spacers:

1) HOOC—$(CH_2)_n$—COOH, where n=1-12, suitable for insertion at the amino terminal end of a peptide, to connect it with a linker on a drug molecule.

2) HO—$(CH_2)_n$—COOH, where n>10, suitable for attachment at the amino terminal of a peptide to connect the L chain with a linker on a Drug molecule.

3) $(C_6H_6)_n$, where n>2, suitable for attachment to join the L chain with a linker on the Drug molecule. The benzene rings provide a rigid spacer between the Drug and L chain. Of course, appropriate functional groups, for example as identified by X below, will be present on the benzene rings to link the drug and the L chain.

Two different linker types are envisioned. In the first type, the Drug-Linker-L chain molecule remains intact after introduction into cells. In the second type, the Drug-Linker-L chain molecule is metabolized to free the drug after introduction into cells.

Linkers that Remain Intact after Introduction

In one method, a cysteine residue is attached to the end of the L chain molecule by methods well known in the art. For instance, the gene construct that carries the L chain molecule can be mutated to include a cysteine reside at the N-terminal portion of the protein. A maleimide linker is then attached to the Cysteine residue by well known means.

In a second method, the linker is attached directly to the drug. A Drug-X moiety can have the following groups wherein X is OH, SH, $NH_2$, CONH, $CONH_2$. Of course, the proper group would not be in an active site or sterically hindered. The following reaction would link the Drug-X to the linker molecule.

$$\text{Br}-\text{CH}_2\text{-Linker} \xrightarrow{\text{Drug-X}} \text{Drug-X-CH}_2\text{-Linker}$$

Once the Drug has a linker attached, the following reaction can be used to link the Drug to the Toxin. In this reaction, the toxin has an accessible lysine group that is used as the attachment point for the Drug. As discussed hereinabove, an extra amino acid, such as lysine, can be readily added to the N-terminal portion of the L chain gene and used as the attachment point for a drug. In the following reaction, sodium cyanoborohydride is used to attach the linker to the lysine group on the L chain molecule.

Drug-Linker-CHO $\xrightarrow{\text{NaCNBH}_3}$ Drug-Linker-CH$_2$—NH-Toxin

Toxin-Lys

Drugs that are envisioned for use in the present invention are those that have a free —XH group and that can act as neuroinhibitors. These neuroinhibitors can interfere with the over-production of neurotransmitters in some medical indications such that the nerves will be inhibited from firing. Appropriate drugs with —XH groups are aconitine, adenosine agonists/antagonists, adrenergics, anatoxin A, antiepileptics, baclofen, batiachotoxin, brefeldin A, brevetoxin, captopril, curare, dantrolene, doxorubin, diazepan, grayanotoxin, lidoraine, methocarbamol, methyllycaconitine, neosaxitoxin, physostigmine, psychosine, THA, tetrodotoxin, vesamicol and vigabatum.

Linkers that Cleave after Introduction

Depending on the Drug's mode of action, it may be important for the Drug to be released from the L chain after introduction. In this method, the Drug has a free —XH group that is the active site for synthesis with a linker. The —XH group could be an alcohol, phenol, amine, carboxylic acid or thiol group.

The general formula for linking a Drug to a toxin so that it will be metabolized after introduction is as follows:

DRUG-XH + Linker $\xrightarrow{\text{Maleimide}}$ DRUG-X-LINKER-Maleimide $\xrightarrow{\text{Toxin-SH}}$ DRUG-X-LINKER-Maleimide-Toxin Where X can be O, N/NH, CO$_2$, S, CONH Where the Linker can be A) or B) as detailed below:

The specific reactions with Linkers A or B are shown below.

Our strategy for linking ribozymes to the toxin transporters employs the free amine functional groups on adenosine and guanosine bases for linker attachment. In particular, our approach will be to incorporate modified adenosine or guanosine residues that are modified at their free amine positions with a linker that is in turn bound to the nitrogen position of succinimide. The structures of these modified nucleosides can be diagrammed as:

Sugar-Base-NH-Linker-Succinimide

Ribozymes are conventionally prepared by sequentially linking nucleosides in a defined order. The linking reaction occurs between the sugar moieties of the individual chemical units. Incorporation of a modified nucleoside, as described above, at either the 3' or 5' end of the ribozyme will provide a means for covalently linking to the toxin transporter according to the mechanism described previously.

Although other materials and methods similar or equivalent to those described herein can be used in the practice or testing of the present invention, the preferred methods and materials are now described. General references for methods that can be used to perform the various PCR and cloning procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987).

Figure 1B:
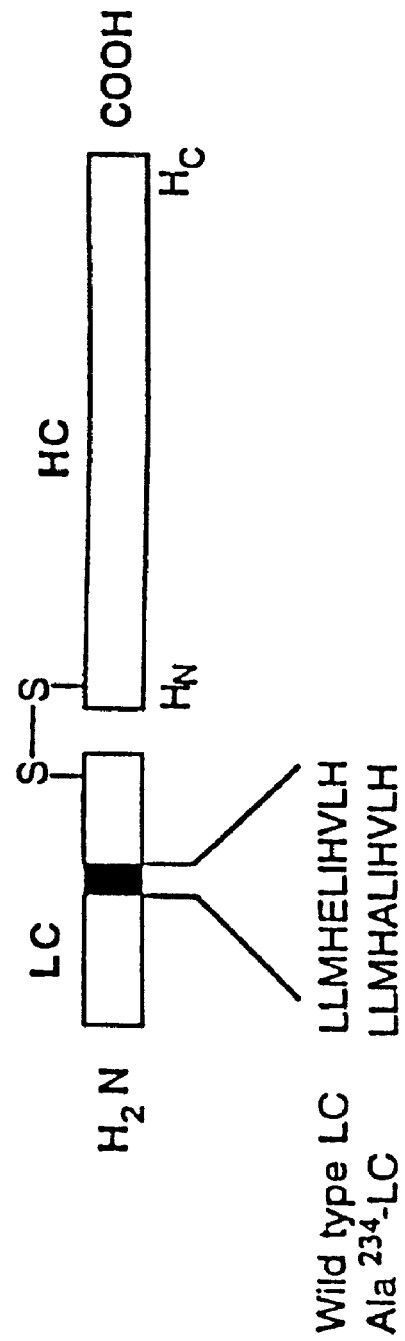
FIG. 1B shows the H chain is disulfide bonded to the L chain. The location of the zinc-binding domain is also diagrammed for the wild type LC (SEQ ID NO: 15) and the Ala$^{234}$-LC (SEQ ID NO: 16).

The initial step in creating an inactivated TeTx composition involved subcloning of the wild-type and mutated L chain structural genes into plasmid expression vectors. The vector employed for this purpose was designed to express a fusion protein that links a maltose binding protein domain at the N terminus, with L chain sequences at the C terminus. A vector-encoded factor $X_a$ proteolytic cleavage site is interposed between the MBP and L chain insert sequences. Site-directed mutagenesis of the L chain DNA was employed to change $Glu^{234}$ to Ala (FIG. 1B).

Example 1 describes the methods used to create recombinant plasmids that encoded maltose-binding fusion proteins of wild-type and mutant tetanus toxin L chain.

EXAMPLE 1

Preparation of Maltose-Binding-Protein-TeTx-L Chain Constructs

*E. coli* K-12 strain TG1 was used as a host for the propagation of all plasmid constructs described below. Plasmid pMAL-LC (wild-type L chain gene) was constructed by polymerase chain reaction (PCR) amplification of a 1417-bp fragment encoding L chain from plasmid pTet87 that has been described by Fairweather et al., in *FEBS Lett.* 323:218 (1993). The two polynucleotide primers, called a and d, that were employed in this PCR amplification had the sequences 5'-GAGATGGTCGACATGCCAATAACCATAAATAAT-3' (SEQ ID NO: 1) and 5'-ACGCGAAGCTTTTATCATG-CAGTTCTATTATA-3' (SEQ ID NO: 2), respectively. The amplification product of this reaction was digested with SalI and HindIII (Promega) and then ligated to vector pMAL-c2 (New England BioLabs) (FIG. 1A) that had been digested with the same enzymes to create the plasmid, pMAL-LC, which harbored wild-type TeTx sequences. For site-directed mutagenesis, two additional primers, b and c, were used that had the sequences 5'-TAGTACATGTATAAGTGCGTGCAT-TAATAG-3' (SEQ ID NO: 3) and 5'-TTATACATGTACTA-CATGGT-3' (SEQ ID NO: 4), respectively. Each of these primers possessed AflIII cleavage sites that were used to mutate a Glu codon to an Ala codon at amino acid position 234 of the TeTx-L chain. PCR amplification of pTet87 was accomplished with primer pairs a/b and c/d, used separately. The amplification product from pair a/b was digested with SalI and AflIII, and that from pair c/d was digested with AflIII and HindIII. After purification with the MAGIC DNA CLEAN-UP SYSTEM (Promega), the samples were ligated to pMAL-c2 that had been cleaved with SalI and HindIII, to create the plasmid, pMAL-LC-Ala$^{234}$, which harbored the mutated TeTx sequence.

After subcloning, plasmid DNA was purified from cultures of ampicillin-resistant transformants, and the structures of the constructs confirmed using restriction mapping and DNA sequencing of the insert. A SalI and HindIII digest yielded a fragment having the expected length of 1417 bp as determined by agarose gel electrophoresis. DNA sequencing confirmed that the nucleotide sequence at the junction of the 5'-end of the L chain gene, the multiple cloning site (MCS), the factor $X_a$ cleavage site, the L chain and the MBP coding sequences were all in the correct reading frame (FIG. 1A).

The availability of the plasmid constructs described above enabled the production of recombinant wild-type and mutant L chain fusion proteins. Specifically, cultures of bacterial clones that harbored plasmids pMAL-LC or pMAL-LC-Ala$^{234}$ were induced with isopropyl β-D-thiogalactoside (IPTG) to stimulate high level synthesis of the recombinant fusion proteins. Large-scale purification of the two fusion proteins was accomplished by affinity chromatography of bacterial extracts on amylose affinity resin.

Example 2 describes the techniques used to produce and purify recombinant L chain fusion proteins encoded by the plasmid constructs described in the previous Example.

EXAMPLE 2

Expression of TeTx Fusion Proteins and Purification of Wild-Type and Ala$^{234}$-L Chain Mutant Proteins

*E. coli* clones harboring plasmids pMAL-LC or pMAL-LC-Ala$^{234}$ were grown to densities of roughly $2 \times 10^8$ cells/ml ($A_{600}$~0.5) at 37° C. in L-broth that was made 100 μg/ml ampicillin and 2 mg/ml glucose. Induction was initiated by the addition of IPTG to a final concentration of 0.3 mM. Cells were harvested 2 hours later by centrifugation at 6000× g for 30 minutes. The resulting pellets were then resuspended in column buffer [10 mM Tris-HCl, 200 mM NaCl, 1 mM ethylene glycol bis(β-aminoethyl ether)-N,N,N',N'-tetraacetic acid, and 1 mM dithiothreitol (DTT) (pH 7.4)] containing 1 mM phenylmethanesulfonyl fluoride (PMSF) and lysed by sonication. After centrifugation, crude extracts were applied to an amylose affinity column (2.5×10 cm, 40 ml of resin). Following the removal of nonbound proteins by washing with buffer, the bound MBP-LC fusion proteins were eluted with column buffer containing 10 mM maltose according to the procedure described by Maina et al., in Gene 74:365 (1988). The isolated fusion proteins were concentrated to 0.5-1 mg/ml using an Amicon CENTRICON. Protein samples were then analyzed by sodium dodecyl sulfate polyacrylamide gel electrophoresis (SDS-PAGE) and Western blotting, using anti-MBP polyclonal and anti-L chain monoclonal antibodies. SDS-PAGE of both cell extracts indicated the presence of an induced protein band ($M_r$~90,000) that was absent from the coomassie staining pattern of the noninduced cultures. The molecular weight of the protein band was in accordance with that expected from a fusion of MBP and L chain ($M_r$~40,000 and 50,000, respectively). The optimal conditions established for expressing recombinant L chain and Ala$^{234}$ mutant using the pMAL-c2 vector system were 2 hours of induction with IPTG at 37° C. Neither a longer induction time nor the inclusion of protease inhibitors increased the product yield. Both fusion proteins were soluble in aqueous buffer (up to 0.5 mg/ml) and stable for up to 8 months when stored at −20° C.

After this initial purification step, both MBP-L chain preparations were cleaved at 23° C. for 24 hours with factor $X_a$ at an enzyme:protein ratio of 0.5-1:100 (w/w). This cleavage gave complete conversion of the fusion proteins to the respective wild-type L chain and $Ala^{234}$-L chain with the liberation of MBP, as confirmed by SDS-PAGE. After extensive dialysis against the column buffer to remove maltose, L chain or $Ala^{234}$-L chain was further purified by reabsorption onto a new affinity column. The desired product from this purification step was found in the column wash fraction. Fractions of the column wash were monitored for $A_{280\ nm}$ and checked again by SDS-PAGE and Western blotting.

For amino acid sequencing, recombinant wild-type or mutant L chains were run on SDS-PAGE and transferred onto a poly(vinylidene difluoride) membrane as described by Tous et al., in *Anal. Biochem.* 179:50 (1989), with automated Edman degradation performed on a Model 4000 protein sequencer (Chelsea Instruments, London). Microsequencing of the two products revealed four residues identical to those of the N-terminus of native L chain preceded by the 11 amino acids encoded by the multiple cloning site of the vector as depicted in FIG. 1A. Given this success in producing recombinant L chain proteins having the desired structures, we next tested the enzymatic activities of these compositions.

Measurement of the zinc-dependent protease activity of native L chain was employed as an assay for the activity of the recombinant L chain proteins. Two different protein substrates were used in this assay. In the first case, bovine small synaptic vesicles (SSVs) were used. The assay for proteolytic cleavage of the substrate was based on coomassie staining and Western blotting of protein gels.

Example 3 describes the techniques used to assess the proteolytic activities of wild-type and mutant recombinant L chain proteins using SSVs as the substrate.

EXAMPLE 3

Measurement of TeTx-L Chain-Dependent Proteolysis of In Vitro Substrates

Native, recombinant wild-type or $Ala^{234}$ L chains were incubated with bovine small synaptic vesicles (SSVS) (0.5 mg/ml) for 90 minutes at 37° C. in 50 mM HEPES, 400 mM NaCl, 5 mM DDT, 2 µM $ZnSO_4$ (pH 7.4). Reactions were terminated by the addition of SDS-PAGE sample buffer followed by boiling for 3-5 minutes. Samples were then subjected to SDS-PAGE and detected by Western blotting using affinity-purified anti-HV62 antibody raised against a 62-amino acid synthetic polypeptide corresponding to residues 33-94 of human VAMP 2 as defined by Shone et al., in *Eur. J. Biochem.* 217:965 (1993). The method used to prepare the anti-HV62 antibody was essentially identical to the method described by de Paiva et al. in *J. Neurochem.* 61:2338 (1993). Incubation of the recombinant (100 nM) or authentic (50 nM) L chain proteins with bovine SSVs resulted in proteolytic cleavage of VAMP, as semi-quantitatively assessed by Western blotting with the anti-VAMP antibody probe or protein staining of the digests following SDS-PAGE. The $Ala^{234}$-L chain proved inactive as a protease, even at a concentration of 2.3 µM. This result confirmed that $Glu^{234}$ is essential for enzymatic activity of the TeTx-L chain.

To more accurately quantitate the relative activities of the native and recombinant L chains, RP-HPLC was used to measure the cleavage of a synthetic 62-residue polypeptide, HV62, corresponding to residues 33-94 of human VAMP-2.

Example 4 describes the procedure that was used to quantify the in vitro activities of native and recombinant L chains using the HV62 peptide substrate.

EXAMPLE 4

Quantitation of the Proteolytic Activities of Native and Recombinant TeTx-L Chain Proteins A stock solution of HV62 peptide (40 µM final concentration, 60 µl final volume) in 20 mM HEPES and 200 mM NaCl (pH 7.4) containing 5 mM DTT was incubated at 37° C. with L chain preparations (100 nM final concentration). At timed intervals, the reactions were terminated by the addition of 60 µl of 5 mM ethylenediamine-tetraacetic acid (EDTA) and 1% (v/v) trifluoroacetic acid (TFA) (pH 2) followed by centrifugation. Samples were stored at −20° C. until analysis. The extent of HV62 hydrolysis was measured by reverse-phase high-pressure liquid chromatography (RP HPLC) on a Micropax $C_{18}$ column equilibrated in 0.05% TFA using a 0-60% acetonitrile gradient, while monitoring at $A_{220\ nm}$. N-Terminal sequencing of the cleavage product confirmed a single proteolytic site between $Gln^{76}$ and $Phe^{77}$, in accordance with the observations of Schiavo et al., as presented in *EMBO J.* 11:3577 (1992). The percentage of HV62 hydrolysis was calculated from the peak height of the breakdown product that corresponded to residues 77-94. A linear standard curve that related peak height to known quantities of product was used for quantitation.

Figure 2:
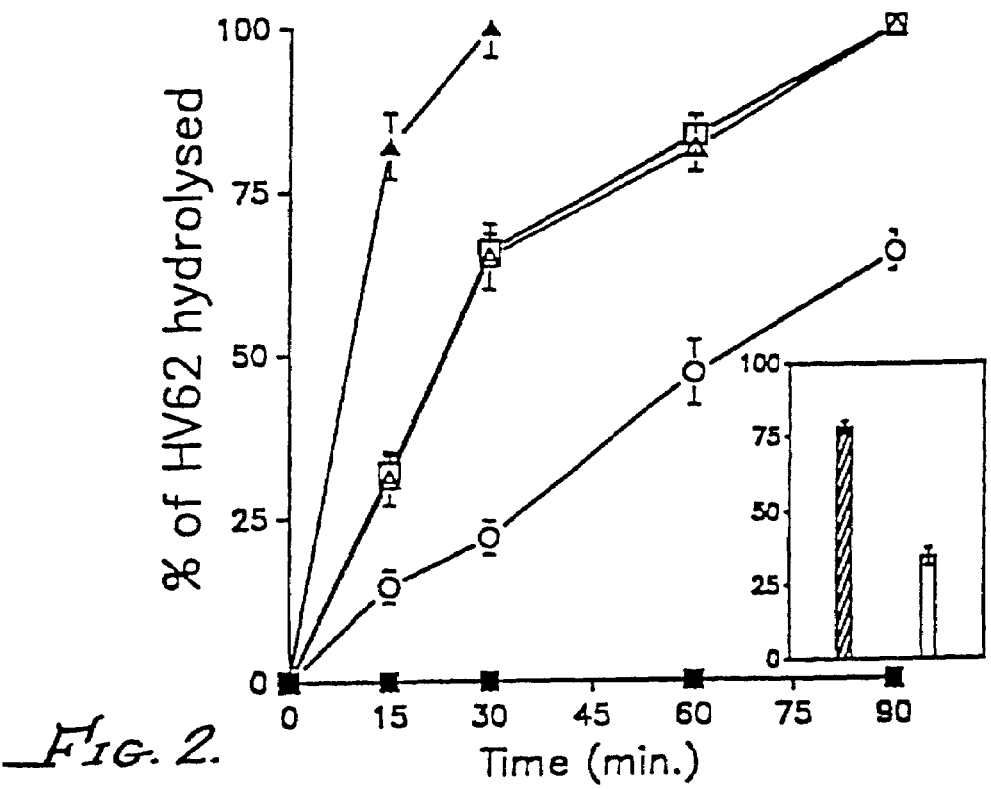
FIG. 2 is a graph showing the percentage of HV62 peptide (a synthetic fragment of human VAMP) cleaved by native, recombinant or mutant L chains as a function of time. The different symbols represent 33 (○), 100 (□) and 250 nM (▲) of native L chain; or 250 nM recombinant L chain (Δ); or 2.5 μM Ala$^{234}$-L chain (■). The inset shows the ability of Ala$^{234}$-L chain to reduce the apparent hydrolysis of HV62 substrate by native L chain. The open bar represents the % substrate hydrolyzed by native L chain in the presence of Ala$^{234}$-L chain, while the hatched bar represents % substrate hydrolyzed in the absence of Ala$^{234}$-L chain.

Quantitation of the separated cleavage product (residues 77-94), time- and concentration-dependent hydrolysis of the polypeptide by native L chain is presented in FIG. 2. Cleavage of the HV62 substrate (40 µM) by recombinant L chain (250 nM) confirmed its proteolytic activity. However, a 2.5-fold higher concentration of the recombinant L chain was required to elicit the same level of hydrolysis (n=4) as that observed for the authentic L chain protein. Under the specified conditions, the initial rates (n=4) of substrate cleavage at 37° C. with 100 nM native and recombinant L chain were 45.6±3.6 and 21.6±2.4 pmol/min, respectively. More importantly, proteolysis of the polypeptide (40 µM) was undetectable when $Ala^{234}$-L chain was incubated for 3 hours at 2.5 µM. This latter finding confirmed that $Glu^{234}$ was essential for catalytic activity of the TeTx-L chain.

The lack of proteolytic activity which characterized the $Ala^{234}$-L chain mutant could either result from an inability of the L chain to bind the substrate or to cleave the peptide bond (Gln Phe). To distinguish between these possibilities, the $Ala^{234}$ L chain was investigated for the ability to attenuate cleavage of the HV62 substrate by native L chain. This was simply tested by preincubating HV62 with $Ala^{234}$ L chain before the addition of native L chain. To make this test, 9 µM HV62 was preincubated with 4.5 µM $Ala^{234}$-L chain in reaction buffer at 37° C. for 1 hour before the addition of 150 nM native L chain. At the end of the reaction period, the sample was analyzed for substrate cleavage as described above. The results from this procedure indicated that the presence of the $Ala^{234}$-L chain mutant protein reduced the activity of the native L chain by more than 50% (FIG. 2, inset). This result indicated the mutant L chain retained the ability to bind peptide, thereby inhibiting the proteolytic activity of the native L chain.

Given the demonstration that $Ala^{234}$-L chain possessed no detectable proteolytic activity, we proceeded to investigate the properties of dichain molecules assembled from native H chain and inactive L chain components. Since the H chain portion of the toxin contributes largely to binding cell surface receptors, we reasoned that a dichain toxin which had lost the ability to proteolyze substrates would conceivably retain the ability to bind at the cell surface and be internalized. Such a dichain species could readily be adapted for use as a vehicle for the delivery of various chemical species to neuronal cells.

Example 5 describes the method used to prepare TeTx dichains that incorporate either native L chain, recombinant wild-type L chain or $Ala^{234}$-L chain.

EXAMPLE 5

Reassociation of TeTx from Native H Chain and Recombinant L Chain

Native H chain, purified from TeTx as detailed by Weller et al., in *Eur. J. Biochem.* 182:649 (1989), was combined with an equimolar amount of either native L chain, recombinant wild-type L chain or $Ala^{234}$-L chain. The mixtures were dialyzed against 2 M urea, 20 mM DTT, 1 M NaCl, and 50 mM Tris-HCl (pH 8.4) with stirring for 18 hours and then further dialyzed without agitation against 50 mM Tris-HCl and 600 mM glycine (pH 8.4) for 72 hours. An aliquot (300 µg) was loaded onto an HPLC DEAE column in 25 mM Tris-HCl buffer (pH 8.4) and eluted with an NaCl gradient (0-1 M) in the same buffer. The extent of covalent reconstitution was checked by nonreducing SDS-PAGE and silver staining.

The reassociation of dichain species was confirmed by virtue of the presence of stained high $M_r$ protein bands that comigrated with native TeTx. With respect to recombinant wild-type and mutant L chains, the relative amounts of the dichain species were 55.1 and 56.8%, respectively, as determined by densitometric scanning of the silver-stained gel. Native H chain and L chain gave similar levels of reconstitution. The latter involved interchain disulfide formation as the toxin was converted back to free H chain and L chain upon reduction by DTT.

With the availability of reassociated dichain toxin molecules, we proceeded to investigate to biological activities of dichains that incorporated recombinant L chains. Although the results of our SDS-PAGE analysis indicated that dichain species had reassociated, this alone was not evidence that the reconstituted proteins were properly folded or that the appropriate inter- and intra-chain disulfide bonds had formed to produce active toxins. Thus, it was necessary to perform a functional assay for toxin activity.

Example 6 describes the methods used to assess the biological activity of the reassociated dichain toxins.

EXAMPLE 6

Bioassay of Reassociated TeTx Dichain Toxins

Mice (20 g) were injected (200 µl/mouse) subcutaneously into the dorsal neck region with dichain toxin or other samples as described by Fairweather et al., in *Infect. Immunol.* 58:1323 (1990), and $LD_{50}$ values were determined as described by Maisey et al., in *Eur. J. Biochem.* 177:683 (1988). The results of this procedure are presented in Table 2.

TABLE 2

Mouse Lethalities of TeTx and Reconstituted Samples Formed from Native HC and Recombinant LC or the $Ala^{234}$ Mutant

| sample | lethality in mice $(LD_{50}/mg)^a$ | covalent dimer$^b$ (%) |
|---|---|---|
| TeTx | $0.5 \times 10^8$ | 100 |
| reconstituted using | | |
| native HC and LC | $3.3 \times 10^8$ | 55.4 |
| native HC and recombinant LC | $3.3 \times 10^5$ | 55.1 |
| native HC and $Ala^{234}$-LC | <50 | 56.8 |
| native HC alone used for reconstitution | <50 | |

$^a$Measured over 4 days, as outlined in the Experimental Procedures, mean values are shown for triplicate experiments.
$^b$HC purified from TeTx was reconstituted with equimolar amounts of native LC, recombinant LC, or $Ala^{234}$-LC to form dichains. The proportion of total protein present as a covalent dimer was determined by SDS-PAGE end densitometric scanning of silver-staining gels.

The results in Table 2 clearly indicate the dichain species reconstituted from the $Ala^{234}$-L chain and native H chain had no toxic activity beyond that of the H chain alone. This absence of activity was not due to the reassociation process because the dichain reconstituted from native H chain and the recombinant L chain exhibited toxicity.

The documented local action of TeTx in blocking neuromuscular transmission that has been described by Habermann et al., in *Naunyn-Schmiedeberg's Arch. Pharmacol.* 311:33 (1980) was also exploited to assess the activities of reconstituted samples relative to that of the intact toxin.

Example 7 describes the methods used to assess the ability of reconstituted dichain toxins to effect neuromuscular transmission.

EXAMPLE 7

Figure 3:
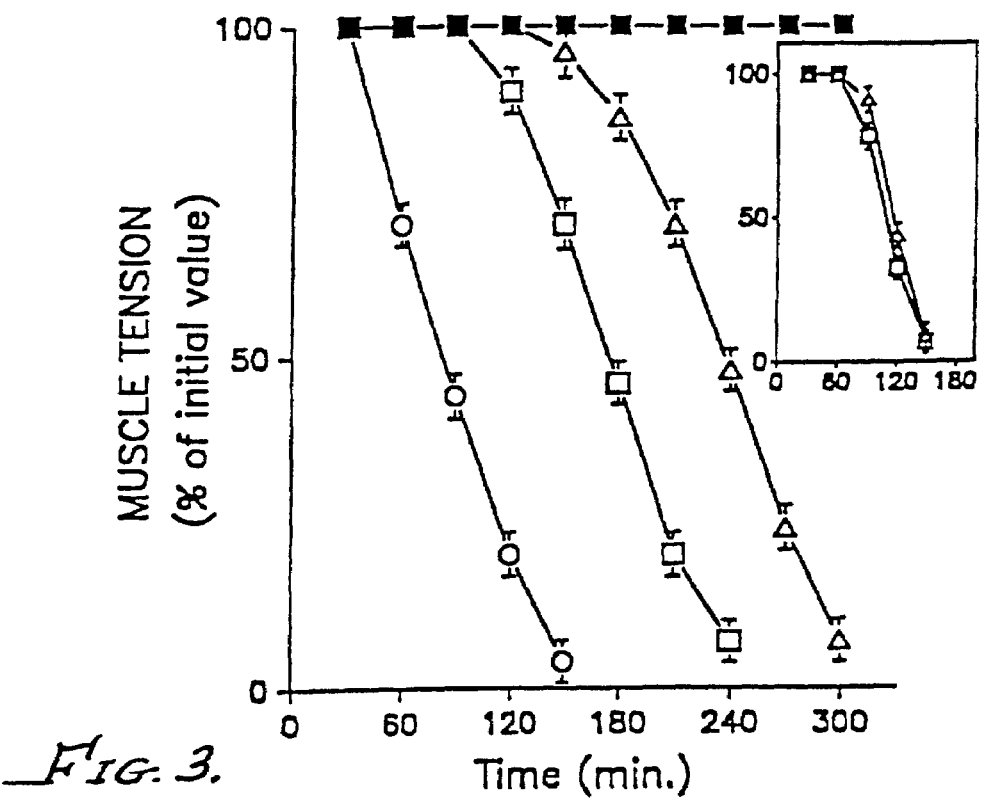
FIG. 3 shows a graph representing muscle tension (as % of an initial value) as a function of time as an assay of neuromuscular transmission. The different symbols represent 10 nM TeTx (○), 10 nM reconstituted native H chain and L chain (□), 10 nM recombinant L chain assembled with native H chain (Δ), 100 nM Ala$^{234}$-L chain refolded with H chain (■). Values are the means (±SD) obtained from 3 experiments. The inset shows the results obtained with 20 nM reconstituted native H chain and L chain (□) and 40 nM reconstituted native H chain and recombinant L chain (Δ). Note that the stated concentrations of reconstituted samples have not taken into account the minor content of noncovalently linked chains.

Effects of Reconstituted H Chain and Recombinant TeTx-L Chain or $Ala^{234}$-L Chain on Neuromuscular Transmission The inhibition of acetylcholine release by the reconstituted dichain from mouse left phrenic nerve-hemidiaphragm preparations was measured as a reduction of the nerve-evoked muscle tension as described by de Paiva et al., in *FEBS Lett.* 277:171 (1990). The time to paralysis was recorded as the period from the addition of toxin to the point when muscle tension decreased to 10% of the original amplitude. The method employed in this procedure has generally been described by de Paiva et al. in *J. Neurochem.* 61:2338 (1993). Results from this procedure are presented in FIG. 3.

At 10 nM, TeTx abolished nerve-evoked muscle tension within 150 minutes, whereas toxin generated from native H chain and L chain required 240 minutes to achieve paralysis. This result was consistent with the reported lower neuromuscular blocking activities of reconstituted chains from TeTx and BoNT/A, relative to those of their native toxins as determined by Weller et al., in *Eur. J. Biochem.* 182:649 (1989), and Maisey et al., in *Eur. J. Biochem.* 177:683 (1988). When recombinant TeTx-L chain was reassembled with native H chain, the resultant dichain exhibited about one-half the expected potency; 40 nM recombinant dichain required the same paralysis time as 20 nM reconstituted native dichains (FIG. 3, inset), consistent with the reduced enzymatic activity of expressed L chain noted above. With the mouse bioassay, TeTx also proved more toxic (15-fold) than the refolded native chains (Table 2). Further, when recombinant wild-type L chain was employed in the reconstitution, there was a further drop in lethality (Table 2), approximating the levels reported by Fairweather et al., in *FEBS Lett.* 323:218.

Most significantly, the dichain toxin reconstituted using Ala$^{234}$-L chain and native H chain proved inactive on neuromuscular transmission over 6 hours at 100 nM. These findings confirmed an essential role for the enzymatic activity in the toxin's action.

Example 8 describes how the native or recombinant Clostridial toxin L chain proteins can be covalently linked to a chemical compound. In this Example, a drug that blocks uptake of acetylcholine from the cytoplasm to the synaptic vesicle is linked to the transporter protein using free SH groups. The synthetic pathway employed in this procedure is outlined in FIG. 4.

EXAMPLE 8

Chemical Bonding of Transporter Protein and Vesamicol

Figure 4:
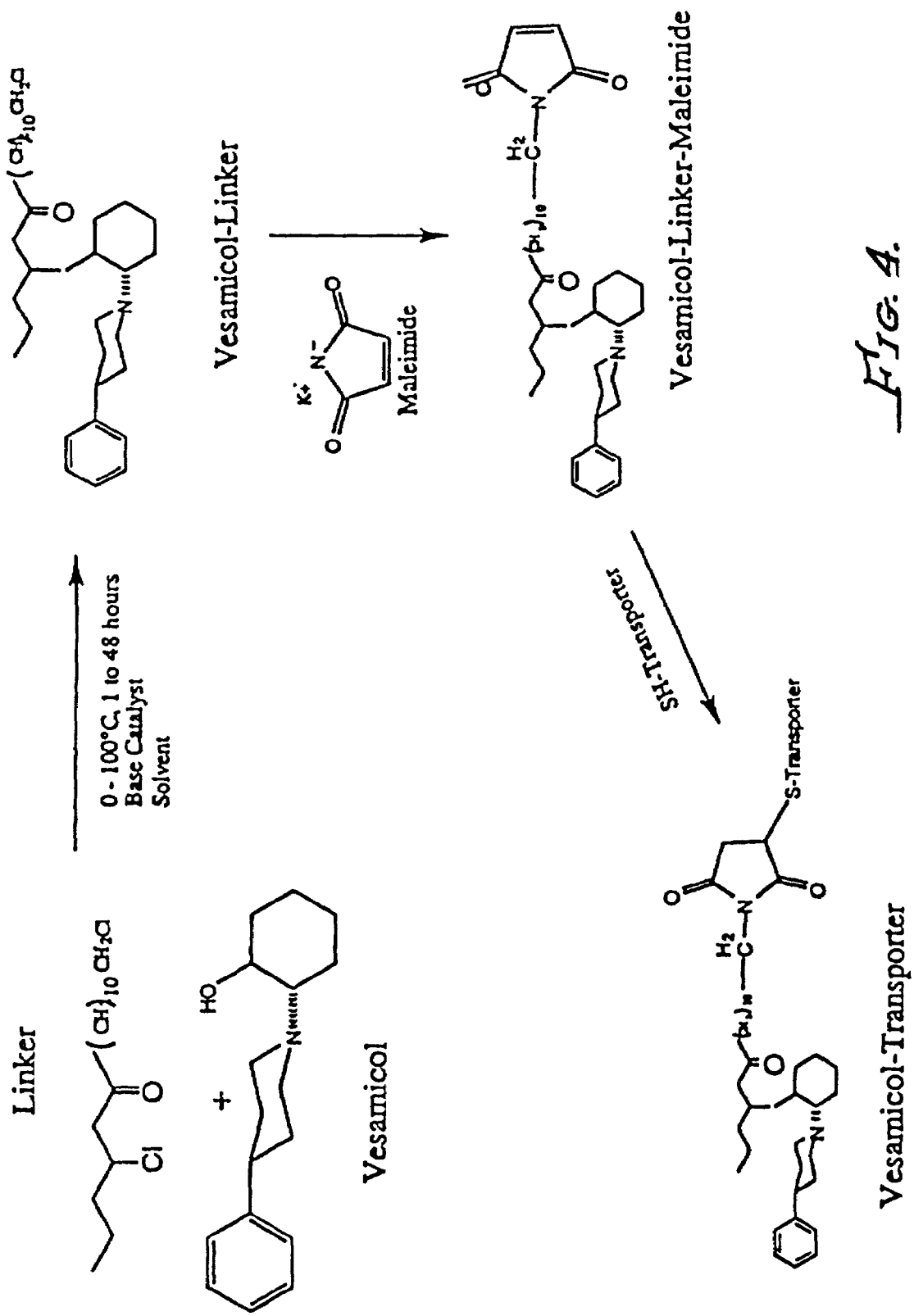
FIG. 4 is a schematic representation of the chemical synthetic scheme used to link the transporter protein and a drug molecule.

Vesamicol is first attached onto a linker of 1-chloropropyl 12-chloro-dodecanoate, using equimolar concentrations of each in a base catalyst solution (such as pyridine, 2,6-dimethylpyridine, triethylamine or tetramethylguanidine) in solvents such as THF, DMSO, DMF or acetonitrile (FIG. 4). The reaction is performed at temperatures of between 0 and 100° C. for from 1 to 48 hours. The resulting vesamicol-linker product is then reacted with equimolar amounts of the potassium salt of maleimide in the same solvents, as above, and in the presence of sodium iodide (used as a catalyst) using similar times and temperatures as above.

The recombinant inactive L chain and native H chain are renatured to produce a dichain molecule of roughly 150 kDa $M_r$. Renaturation is accomplished by mixing equimolar amounts of L chain and H chain proteins in the presence of urea and DTT. The mixture is dialyzed at 4° C. against a buffer that had the same composition as the dialysis buffer employed in Example 5. The buffer is preferably oxygenated during the renaturation process. The buffer is changed 5 times over 24 hours. The removal of urea and DTT leads to the disulfide linkage of the L chain and H chain. Each dichain has several free sulfhydryl groups that are available for drug attachment.

The vesamicol linker is bonded to the free sulfhydryl groups found on the intact transporter molecule by mixing a 5 fold molar excess of the vesamicol linker with the transporter in Tris-NaCl, described above, at 4° C. in the dark for 1 to 24 hours. The transporter-vesamicol preparation is then dialyzed against Tris-NaCl overnight to remove excess vesamicol-linker-maleimide from the vesamicol transporter.

The drug-transporter material is then available for administration as a sterile injection in a therapeutically effective dose.

The modified and inactivated TeTx neurotoxin transporter described above will have numerous clinical applications. For example, we anticipate these modified toxins will be useful in the treatment of neuromuscular disorders that affect spasticity in general areas of the body. These disorders include, but are not limited to, spasmodic torticollis, post-stroke or traumatic brain injury induced spasticity.

Example 9 describes how the chemically modified, inactive TeTx transporter described above can be used as a therapeutic agent for delivering chemical compounds to neurons that express toxin receptors.

EXAMPLE 9

Therapeutic Administration of Modified Toxins

Spasmodic Torticollis (Cervical Dystonia)

A female, age 45, suffering from spasmodic Torticollis, as manifested by spasmodic or tonic contractions of the neck musculature, producing stereotyped abnormal deviations of the heard, the chin, being rotated to one side, and the shoulder being elevated toward the side at which the head is rotated, is treated by therapeutically effective doses of an appropriate drug, as would be appreciated by one of ordinary skill in the art, attached to an inactive tetanus toxin transporter directly into the affected muscles. After 3-7 days, the symptoms are substantially alleviated, i.e., the patient is able to hold her head and shoulder in a normal position or there is a dramatic reduction in the pain and discomfort.

Example 10 further illustrates how the chemically modified, inactive TeTx transporter described above can be used as a therapeutic agent for delivering chemical compounds to neurons that express toxin receptors.

EXAMPLE 10

Therapeutic Administration of Modified Toxins

Post Stroke or Traumatic Brain Injury Induced Spasticity

A young male, age 24, suffering from traumatic brain injury, has developed upper and lower limb spasticity which restricts movement and impedes rehabilitation and hygiene. Symptoms include severe closing of the hand and curling of the wrist and closing of the legs such that the patient and attendant have difficulty with hygiene. In addition, the spastic nature of the limb impedes physical rehabilitation and causes muscle contracture and possibly joint immobilization. Sterile injections of therapeutically effective doses of an appropriate drug, as would be appreciated by one of ordinary skill in the art, attached to an inactive tetanus toxin transporter are administered directly into the affected muscles. Relief of these symptoms occur in 7-21 days such that the lower limbs have relaxed enough to allow the patient and attendant to perform normal hygiene.

A female, age 70, suffering from a cerebral vascular event (stroke) has developed lower limb spasticities which require extensive efforts to maintain hygiene. The patient is injected in both limbs with therapeutically effective doses of an appropriate drug, as would be appreciated by one of ordinary skill in the art, attached to an inactive tetanus toxin transporter. Injections are made directly into the affected muscles. Relief of these symptoms occur in 7-21 days such that the lower limbs have relaxed enough to allow the patient and attendant to perform normal hygiene.

Whereas the foregoing descriptions, results and conclusions have primarily regarded the production, characterization and use of the modified TeTx transporter, parallel discoveries have been made with respect to a modified BoNT/A transporter. Our work with BoNT/A began with the subcloning of the L chain protein coding sequence.

A DNA fragment encoding the BoNT/A-L chain was PCR-amplified using sense and antisense primers that annealed to the 5' and 3' ends of the BoNT/A-L chain gene. The amplification product was ligated into the pBluescript II SK+ vector to create the plasmid, pSAL. As described in the following Example, double-stranded plasmid sequencing verified that the nucleotide sequence of the cloned L chain gene was identical to that of the authentic BoNT/A-L chain gene.

Example 11 describes the methods used to clone the polynucleotide sequence encoding the BoNT/A-L chain.

EXAMPLE 11

Subcloning the BoNT/A-L Chain Gene

The DNA sequence encoding the BoNT/A-L chain was amplified by a PCR protocol that employed synthetic oligonucleotides having the sequences, 5'-AAAGGCCTTTTGT-TAATAAACAA-3' (SEQ ID NO: 5) and 5'-GGAATTCT-TACTTATTGTATCCTTTA-3' (SEQ ID NO: 6). Use of these primers allowed the introduction of Stu I and EcoR I restriction sites into the 5' and 3' ends of the BoNT/A-L chain gene fragment, respectively. These restriction sites were subsequently used to facilitate unidirectional subcloning of the amplification products. Additionally, these primers introduced a stop codon at the C-terminus of the L chain coding sequence. Chromosomal DNA from *C. botulinum* (strain 63 A) served as a template in the amplification reaction.

The PCR amplification was performed in a 100 µl volume containing 10 mM Tris-HCl (pH 8.3), 50 mM KCl, 1.5 mM $MgCl_2$, 0.2 mM of each deoxynucleotide triphosphate (dNTP), 50 µmol of each primer, 200 ng of genomic DNA and 2.5 units of Taq-polymerase (Promega). The reaction mixture was subjected to 35 cycles of denaturation (1 minute at 94° C.), annealing (2 minutes at 37° C.) and polymerization (2 minutes at 72° C.). Finally, the reaction was extended for an additional 5 minutes at 72° C.

The PCR amplification product was digested with Stu I and EcoR I, purified by agarose gel electrophoresis, and ligated into Sma I and EcoR I digested pBluescript II SK+ to yield the plasmid, pSAL. Bacterial transformants harboring this plasmid were isolated by standard procedures. The identity of the cloned L chain polynucleotide was confirmed by double stranded plasmid sequencing using SEQUENASE (United States Biochemicals) according to the manufacturer's instructions. Synthetic oligonucleotide sequencing primers were prepared as necessary to achieve overlapping sequencing runs. The cloned sequence was found to be identical to the sequence disclosed by Binz, et al., in *J. Biol. Chem.* 265:9153 (1990), and Thompson et al., in *Eur. J. Biochem.* 189:73 (1990).

Site-directed mutants designed to compromise the enzymatic activity of the BoNT/A-L chain were also created.

Example 12 describes the method used to construct polynucleotides encoding mutant BoNT/A-L chains.

EXAMPLE 12

Mutagenesis of the BoNT/A-L Chain Polynucleotide

PCR-mediated mutagenesis of BoNT/A $Glu^{224}$ to Gln or $His^{227}$ to Tyr was performed using the cloned L chain polynucleotide as a template according to a modification of the method described by Higuchi in PCR Protocols, Edited by Innis, Gelfand, Sninsky and White; Academic Press, Inc. (1990). The sense and antisense oligonucleotide primers used to create the $Gln^{224}$ mutant had the sequences, 5'-GCACAT-CAACTTATACAT-3' (SEQ ID NO:7) and 5'-ATG-TATAAGTTGATGTGC-3' (SEQ ID NO:8). The sense and antisense oligonucleotide primers used to create the $Tyr^{227}$ mutant had the sequences, 5'-AACTTATATATGCTGGAC-3' (SEQ ID NO: 9) and 5'-GTCCAGCATATATAAGTT-3' (SEQ ID NO: 10). Secondary PCR, using primers having the sequences of SEQ ID NO:5 and SEQ ID NO:6, amplified the complete mutant genes. The amplified polynucleotide harboring the $Gln^{224}$ mutation was digested with Stu I and EcoR I and ligated to pBluescript II SK+ vector that had been double-digested with Sma I and EcoR I, to create the plasmid, pSAL-$Gln^{224}$.

The amplified polynucleotide harboring the $Tyr^{227}$ mutation was digested with Stu I and EcoR I, and ligated to pBluescript II SK+ vector that had been double-digested with Sma I and EcoR I, to create the plasmid, pSAL-$Tyr^{227}$.

Polynucleotides encoding recombinant L chains were cleaved from their respective plasmids and ligated into prokaryotic expression vectors to facilitate the production of fusion proteins in bacteria. The pMAL-c2 vector was employed to create expression plasmids capable of directing the high level expression of maltose binding fusion proteins. As disclosed in Example 21 (see later), the pGEX-2T vector (Pharmacia) was similarly employed for the production of glutathione S-transferase (GST) fusion proteins with equally good results. Although we have produced and tested the GST fusion proteins, we have found that fusion proteins incorporating maltose binding domains can advantageously be purified with particular ease. The L chain protein coding sequences in all of the expression constructs described herein were under the transcriptional control of vector-borne, IPTG-inducible Pa promoters.

Example 13 describes the methods used to construct plasmids that directed expression of the BoNT/A wild-type and mutant L chains as maltose binding fusion proteins in bacterial host cells.

EXAMPLE 13

Construction of a Recombinant BoNT/A-L Chain Expression Plasmids

Figure 5:
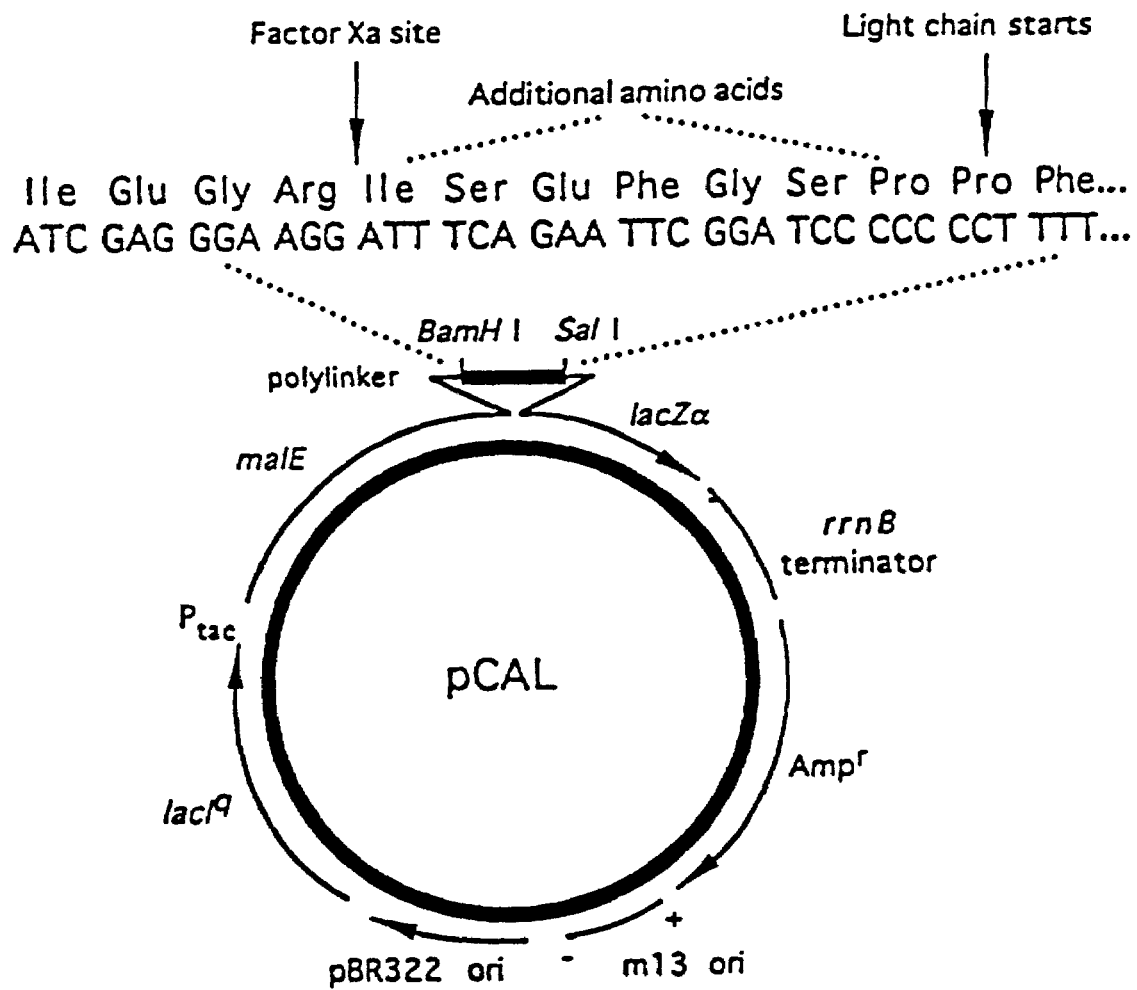
FIG. 5 is a schematic representation of the recombinant BoNT/A light chain expression construct, pCAL. This was produced by insertion of the L chain gene between the BamHI and SalI restriction sites at the polylinker of the vector pMAL-c2. The vector contains the inducible P$_{tac}$ promoter positioned to transcribe the malE-LacZα gene fusion. The lacI$^q$ gene encodes the lac repressor which represses transcription from P$_{tac}$ until induction by isopropyl β-D-thiogalactoside (IPTG). The rrnB terminator prevents transcription from interfering with plasmid replication. Amp$^r$ encodes β-lactamase for ampicillin resistance. M13-ori and pBR322ori indicate the origins of DNA replication. The Factor X$_a$ cleavage site and L chain start are denoted by arrows. The nucleotide sequence (SEQ ID NO: 17) and the encoded amino acid sequence (SEQ ID NO: 18) are shown.

The BoNT/A wild-type and mutant L chain polynucleotides, carried by the pSAL, pSAL-$Gln^{224}$ and pSAL-$Tyr^{227}$ plasmids, were excised by digestion with BamH I and Sal I and then ligated between the BamH I and Sal I sites of the pMAL-c2 expression vector (New England BioLabs) to produce the plasmids pCAL, pCAL-$Gln^{224}$ and pCAL-$Tyr^{227}$. The pCAL plasmid is diagrammed in FIG. 5. The pCAL pCAL-$Gln^{224}$ and pCAL-$Tyr^{227}$ plasmids are identical except for the mutation of single codons as specified above. The pMAL-c2 vector harbors the MalE gene, which encodes the maltose binding protein (MBP), under transcriptional control of the IPTG-inducible $P_{tac}$ promoter. A multiple cloning site (MCS) within this plasmid permitted subcloning of the L chain coding sequences at the 3' end of the MalE coding sequences. Importantly, a Factor $X_a$ protease cleavage sequence was present between the MalE and the L chain sequences of the fusion proteins. Transformed *E. coli* TG1 harboring the expression plasmids were isolated by standard methods.

The structures of the pCAL, pCAL-$Gln^{224}$ and pCAL-$Tyr^{227}$ plasmids were verified by restriction enzyme digestion and agarose gel electrophoresis. DNA sequence analysis confirmed that the inserts present in these plasmids were correctly orientated with respect to the translational reading frame of the authentic L chain gene. Sequence analysis also confirmed that the 5' ends of the L chain genes were fused to the MCS and Factor $X_a$ cleavage sites via short sequences that encoded seven amino acids, as expected. Moreover, the DNA sequencing results indicated that the L chain sequences and the linked MalE sequences were in the same translational reading frames.

With the availability of bacterial clones that harbored expression plasmids encoding the recombinant L chains, it became possible to produce useful quantities of both wild-type and mutant BoNT/A-L chain proteins. Similar procedures were employed for the production and purification of wild-type and mutant L chain fusion proteins. While the following Example presents the procedures employed using the wild-type and $Try^{227}$ mutant fusion proteins, identical methods were applicable to production of fusion proteins harboring the $Gln^{224}$ mutation.

Example 14 describes the methods used to verify expression of the wild-type and mutant L chains in bacteria harboring the pCAL and pCAL-$Tyr^{227}$ plasmids.

EXAMPLE 14

Expression of the BoNT/A-L Chain Fusion Proteins

Well isolated bacterial colonies harboring either pCAL or pCAL-$Tyr^{227}$ were used to inoculate L-broth containing 100 µg/ml ampicillin and 2% (w/v) glucose, and grown overnight with shaking at 30° C. The overnight cultures were diluted 1:10 into fresh L-broth containing 100 µg/ml of ampicillin and incubated for 2 hours. Fusion protein expression was induced by addition of IPTG to a final concentration of 0.1 mM. After an additional 4 hour incubation at 30° C., bacteria were collected by centrifugation at 6,000×g for 10 minutes.

A small-scale SDS-PAGE analysis confirmed the presence of a 90 kDa protein band in samples derived from IPTG-induced bacteria. This $M_r$ was consistent with the predicted size of a fusion protein having MBP (~40 kDa) and BoNT/A-L chain (~50 kDa) components. Furthermore, when compared with samples isolated from control cultures, the IPTG-induced clones contained substantially larger amounts of the fusion protein.

The presence of the desired fusion proteins in IPTG-induced bacterial extracts was also confirmed by Western blotting using the polyclonal anti-L chain probe described by Cenci di Bello et al., in *Eur. J. Biochem.* 219:161 (1993). Reactive bands on PVDF membranes (Pharmacia; Milton Keynes, UK) were visualized using an anti-rabbit immunoglobulin conjugated to horseradish peroxidase (Bio-Rad; Hernel Hempstead, UK) and the ECL detection system (Amersham, UK). Western blotting results confirmed the presence of the dominant fusion protein together with several faint bands corresponding to proteins of lower $M_r$ than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown.

The yield of intact fusion protein isolated by the above procedure remained fully adequate for all procedures described herein. Based on estimates from stained SDS-PAGE gels, the bacterial clones induced with IPTG yielded 5-10 mg of total MBP-wild-type or mutant L chain fusion protein per liter of culture. Thus, the method of producing BoNT/A-L chain fusion proteins disclosed herein was highly efficient, despite any limited proteolysis that did occur.

The MBP-L chain fusion proteins encoded by the pCAL and pCAL-$Tyr^{227}$ expression plasmids were purified from bacteria by amylose affinity chromatography. Recombinant wild-type or mutant L chains were then separated from the sugar binding domains of the fusion proteins by site-specific cleavage with Factor $X_a$. This cleavage procedure yielded free MBP, free L chains and a small amount of uncleaved fusion protein. While the resulting L chains present in such mixtures have been shown to possess the desired activities, we have also employed an additional purification step. Accordingly, the mixture of cleavage products was applied to a second amylose affinity column that bound both the MBP and uncleaved fusion protein. Free L chains were not retained on the affinity column, and were isolated for use in experiments described below.

Example 15 describes the method used to produce and purify both wild-type and $Tyr^{227}$ mutant recombinant BoNT/A light chains from bacterial clones.

EXAMPLE 15

Purification of Fusion Proteins and Isolation of Recombinant BoNT/A-L Chains

Pellets from 1 liter cultures of bacteria expressing either the wild-type or the mutated BoNT/A-L chain proteins were resuspended in column buffer [10 mM Tris-HCl (pH 8.0), 200 mM NaCl, 1 mM EGTA and 1 mM DTT] containing 1 mM phenyl-methanesulfonyl fluoride (PMSF) and 10 mM benzamidine, and lysed by sonication. The lysates were cleared by centrifugation at 15,000×g for 15 minutes at 4° C. Supernatants were applied to an amylose affinity column [2×10 cm, 30 ml resin] (New England BioLabs; Hitchin, UK). Unbound proteins were washed from the resin with column buffer until the eluate was free of protein as judged by a stable absorbance reading at 280 nm. The bound MBP-L chain fusion protein was subsequently eluted with column buffer containing 10 mM maltose. Fractions containing the fusion protein were pooled and dialyzed against 20 mM Tris-HCl (pH 8.0) supplemented with 150 mM NaCl, 2 mM, $CaCl_2$ and 1 mM DTT for 72 hours at 4° C.

Fusion proteins were cleaved with Factor $X_a$ (Promega; Southampton, UK) at an enzyme:substrate ratio of 1:100 while dialyzing against a buffer of 20 mM Tris-HCl (pH 8.0) supplemented with 150 mM NaCl, 2 mM, $CaCl_2$ and 1 mM DTT. Dialysis was carried out for 24 hours at 4° C. The mixture of MBP and either wild-type or mutant L chain that resulted from the cleavage step was loaded onto a 10 ml amylose column equilibrated with column buffer. Aliquots of the flow through fractions were prepared for SDS-PAGE analysis to identify samples containing the L chains. Remaining portions of the flow through fractions were stored at −20° C. Total *E. coli* extract or the purified proteins were solubilized in SDS sample buffer and subjected to PAGE according to standard procedures. Results of this procedure indicated the recombinant toxin fragment accounted for roughly 90% of the protein content of the sample.

The foregoing results indicated that the approach to creating MBP-L chain fusion proteins described herein could be used to efficiently produce wild-type and mutant recombinant BoNT/A-L chains. Further, our results demonstrated that recombinant L chains could be separated from the maltose binding domains of the fusion proteins and purified thereafter. While these results directly addressed certain structural properties of the recombinant L chains, the functional properties of these proteins remained to be determined. Thus, we proceeded to investigate the enzymatic activities of the wild-type and mutant recombinant L chains.

A sensitive antibody-based assay was developed to compare the enzymatic activities of recombinant L chain products and their native counterparts. The assay employed an antibody having specificity for the intact C-terminal region of SNAP-25 that corresponded to the BoNT/A cleavage site. Western Blotting of the reaction products of BoNT/A cleavage of SNAP-25 indicated an inability of the antibody to bind SNAP-25 sub-fragments. Thus, the antibody reagent employed in the following Example detected only intact SNAP-25. The loss of antibody binding served as an indicator of SNAP-25 proteolysis mediated by added BoNT/A light chain or recombinant derivatives thereof.

Example 16 describes the method used to demonstrate that both native and recombinant BoNT/A-L chains, but not $Tyr^{227}$ mutant L chains, can proteolyze a SNAP-25 substrate. Notably, although the $Tyr^{227}$ mutant L chain was employed in this Example, the $Gln^{224}$ mutant L chain gave identical results in the SNAP-25 cleavage assay.

EXAMPLE 16

Evaluation of the Proteolytic Activities of Recombinant L Chains Against a SNAP-25 Substrate A quantitative assay was employed to compare the abilities of the wild-type and mutant BoNT/A-L chains, and their recombinant analogs, to cleave a SNAP-25 substrate. The substrate utilized for this assay was obtained by preparing a glutathione-S-transferase (GST)-SNAP-25 fusion protein, containing a cleavage site for thrombin, expressed using the pGEX-2T vector and purified by affinity chromatography on glutathione agarose. The SNAP-25 was then cleaved from the fusion protein using thrombin in 50 mM Tris-HCl (pH 7.5) containing 150 mM NaCl and 2.5 mM $CaCl_2$ (Smith et al., Gene 67:31 (1988)) at an enzyme:substrate ratio of 1:100. Uncleaved fusion protein and the cleaved glutathione-binding domain bound to the gel. The recombinant SNAP-25 protein was eluted with the latter buffer and dialyzed against 100 mM HEPES (pH 7.5) for 24 hours at 4° C. The total protein concentration was determined by routine methods.

Rabbit polyclonal antibodies specific for the C-terminal region of SNAP-25 were raised against a synthetic peptide having the amino acid sequence, CANQRATKMLGSG (SEQ ID NO:11). This peptide corresponded to residues 195 to 206 of the synaptic plasma membrane protein and an N-terminal cysteine residue not found in native SNAP-25. The synthetic peptide was conjugated to bovine serum albumin (BSA) (Sigma; Poole, UK) using maleimidobenzoyl-N-hydroxysuccinimide ester (MBS) as a cross-linking agent (Sigma; Poole, UK) to improve antigenicity (Liu et al., Biochemistry 18:690 (1979)). Affinity purification of the anti-peptide antibodies was carried out using a column having the antigenic peptide conjugated via its N-terminal cysteine residue to an aminoalkyl agarose resin (Bio-Rad; Hemel Hempstead, UK), activated with iodoacetic acid using the cross-linker ethyl-3-(3-dimethylpropyl) carbodiimide. After successive washes of the column with a buffer containing 25 mM Tris-HCl (pH 7.4) and 150 mM NaCl, the peptide-specific antibodies were eluted using a solution of 100 mM glycine (pH 2.5) and 200 mM NaCl, and collected in tubes containing 0.2 ml of 1 M Tris-HCl (pH 8.0) neutralizing buffer.

All recombinant preparations containing wild-type or mutant L chain were dialyzed overnight at 4° C. into 100 mM HEPES (pH 7.5) containing 0.02% Lubrol and 10 µM zinc acetate before assessing their enzymatic activities. BoNT/A, previously reduced with 20 mM DTT for 30 minutes at 37° C., as well as these dialyzed samples, were then diluted to different concentrations in the latter HEPES buffer supplemented with 1 mM DTT.

Reaction mixtures included 5 µl recombinant SNAP-25 substrate (8.5 µM final concentration) and either 20 µl reduced BoNT/A, recombinant wild-type L chain or $Tyr^{227}$ mutant L chain. All samples were incubated at 37° C. for 1 hour before quenching the reactions with 25 µl aqueous 2% trifluoroacetic acid (TFA) and 5 mM EDTA (Foran et al., Biochemistry 33:15365 (1994)). Aliquots of each sample were prepared for SDS-PAGE and Western blotting with the polyclonal SNAP-25 antibody by adding SDS-PAGE sample buffer and boiling. Anti-SNAP-25 antibody reactivity was monitored using an ECL detection system and quantified by densitometric scanning.

Western blotting results, graphically presented in FIG. 6, indicated clear differences between the proteolytic activities of the purified mutant L chain and either native or recombinant wild-type BoNT/A-L chain. Specifically, recombinant wild-type L chain cleaved the SNAP-25 substrate, though somewhat less efficiently than the reduced BoNT/A native L chain that served as the positive control in the procedure. In contrast, the $Tyr^{227}$ mutant exhibited substantially no proteolytic activity in the assay. Thus, an enzymatically active form of the BoNT/A-L chain has been produced by recombinant means and subsequently isolated. Moreover, substitution of a single amino acid in the L chain protein abrogated the ability of the recombinant protein to degrade the synaptic terminal protein. As disclosed later, we have also discovered the same effect may be achieved by mutating more than one amino acid position within the Clostridial toxin.

As a preliminary test of the biological activity of the wild-type recombinant BoNT/A-L chain, the ability of the MBP-L chain fusion protein to diminish $Ca^{2+}$-evoked catecholamine release from digitonin-permeabilized bovine adrenochromaffin cells was examined. Consistently, wild-type recombinant L chain fusion protein, either intact or cleaved with Factor $X_a$ to produce a mixture containing free MBP and recombinant L chain, induced a dose-dependent inhibition of $Ca^{2+}$-stimulated release equivalent to the inhibition caused by native BoNT/A.

Example 17 describes the methods used to assess the ability of the BoNT/A fusion protein to inhibit catecholamine release from chromaffin cells.

EXAMPLE 17

Assessing the Ability of Recombinant L Chain Fusion Protein to Inhibit Catecholamine Release From Permeabilized Chromaffin Cells Chromaffin cells were prepared from bovine adrenal glands by protease perfusion using the method described by Livett in Physiol. Rev. 64:1103 (1984). The cells were plated at $1 \times 10^6$ cells/well in 24-well plates in Dulbecco's modified Eagle's medium supplemented with 10% fetal calf serum, 8 µM fluorodoxyurine, 50 µg/ml gentamicin, 10 µM cytosine arabinofuranoside, 2.5 µg/ml fungizone, 25 international units/ml penicillin, 25 µg/ml streptomycin and 2 mM glutamine. Experiments were performed 3-8 days after plating. $Ca^{2+}$-evoked catecholamine release was measured fluorometrically.

Figure 7A:
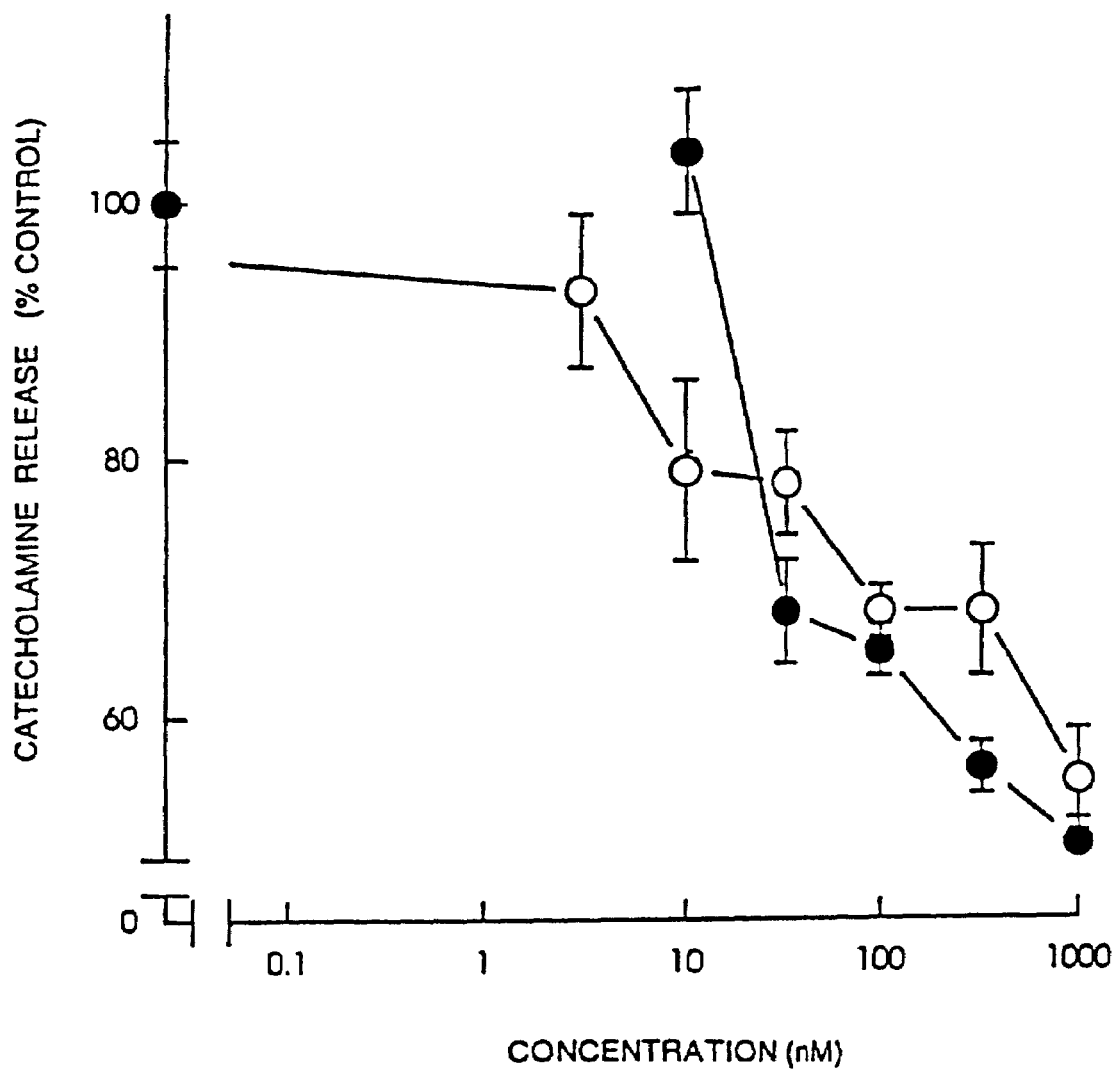
FIGS. 7A and 7B are line graphs illustrating that recombinant L chain or its fusion protein inhibit catecholamine release from permeabilized chromaffin cells.
Figure 7B:
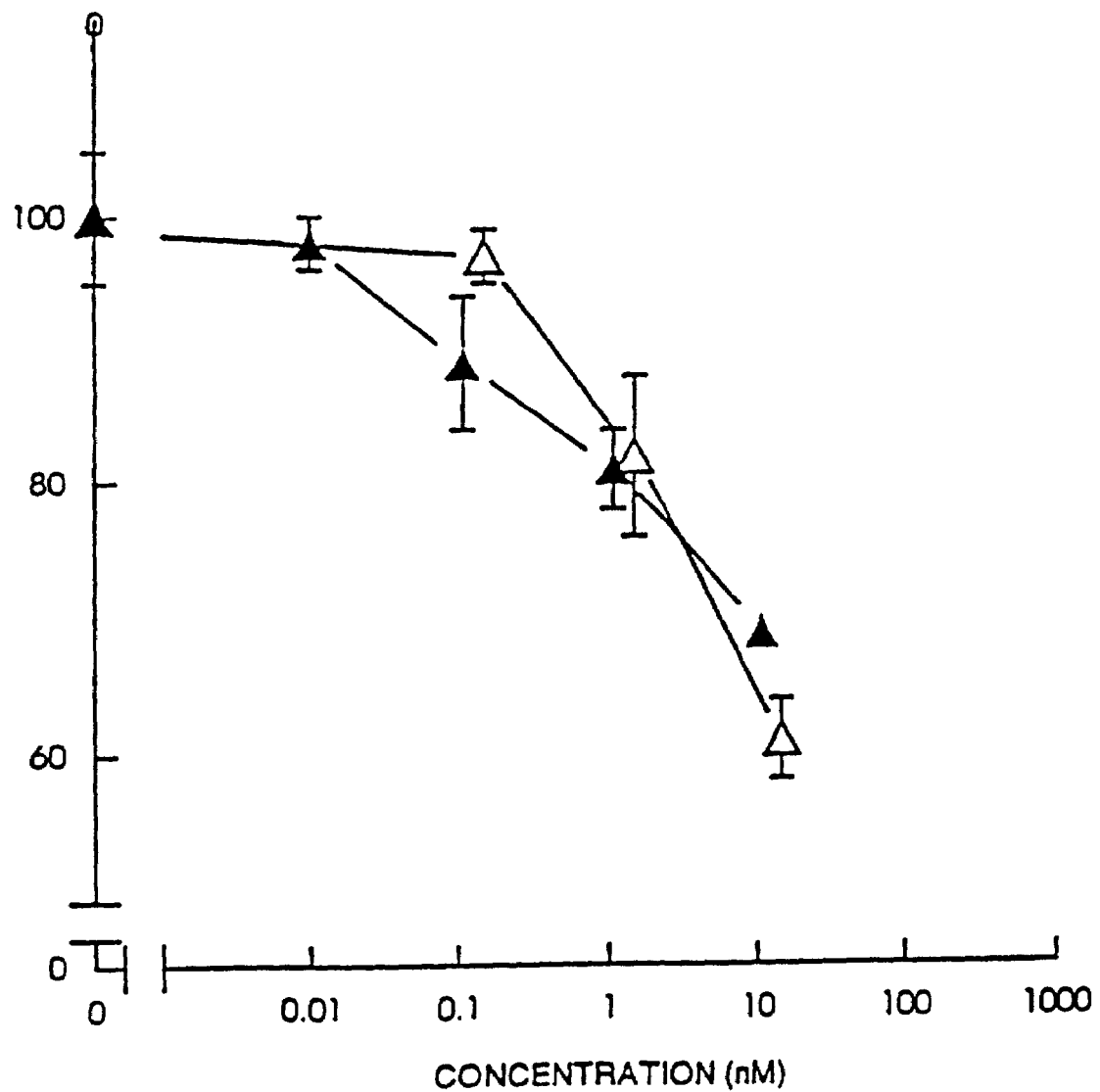

Results of this preliminary test, presented in FIG. 7, indicated that both the recombinant wild-type BoNT/A-L chain fusion protein and a mixture containing the Factor $X_a$ cleavage products of the wild-type recombinant L chain advantageously exhibited biological properties similar to those of the native BoNT/A toxin. It was then of interest to explore whether mutant L chains would be devoid of these properties, as desired.

Given that a single point mutation could eliminate the proteolytic activity of recombinant L chains, we proceeded to reconstitute dichain molecules that incorporated mutant L chains as a means for creating inactive BoNT/A neurotoxins. Purified recombinant wild-type and Tyr[227] mutant L chains, in the absence of the sugar binding domains of the parent fusion proteins, were reconstituted with native H chain isolated from BoNT/A. Formation of the ~150 kDa disulfide-linked dichain toxin was confirmed by SDS-PAGE under non-reducing conditions. Quantitative analysis revealed that the recombinant L chains reassociated with the native H chain protein to form dichains less efficiently than did the native L chain protein. This difference may reflect a divergence between the folded structures of the recombinant and native proteins.

Example 18 describes the method used to reassociate dichain toxins having H and L chains. Dichains incorporating either native, recombinant wild-type or mutant BoNT/A-L chains were reassociated by this procedure. While the Tyr[227] mutant L chain is employed in the Example, those having ordinary skill in the art will appreciate that other mutant L chains can be associated with native H chains by the same procedure.

EXAMPLE 18

Reconstitution of Native L Chain, Recombinant Wild-Type or Tyr[227] Mutant L Chain with Purified H Chain Native H and L chains were dissociated from BoNT/A (List Biologicals Inc.; Campbell, USA) with 2 M urea, reduced with 100 mM DTT and then purified according to established chromatographic procedures (Kozaki et al., *Japan J. Med. Sci. Biol.* 34:61 (1981); Maisey et al., *Eur. J. Biochem.* 177:683 (1988)). Purified H chain was combined with an equimolar amount of either native L chain, recombinant wild-type L chain or the Tyr[227] mutant L chain. Reconstitution was carried out by dialyzing the samples against a buffer consisting of 25 mM Tris (pH 8.0), 50 µM zinc acetate and 150 mM NaCl over 4 days at 4° C. Following dialysis, the association of the recombinant L chain and native H chain to form disulfide-linked 150 kDa dichains was monitored by SDS-PAGE and quantified by densitometric scanning. The proportion of dichain molecules formed with the recombinant L chains was lower than that obtained when native L chain was employed. Indeed, only about 30% of the recombinant wild-type or mutant L chain was reconstituted while >90% of the native L chain reassociated with the H chain. In spite of this lower efficiency of reconstitution, sufficient material incorporating the recombinant L chains was easily produced for use in subsequent functional studies.

Dichain molecules harboring mutant L chains had novel properties when compared with reconstituted dichains having either native or wild-type recombinant L chains in in vitro physiological assays. Following dialysis, the reconstituted material described in the previous Example was applied to the medium bathing excised mouse phrenic nerve-hemidiaphragms. As disclosed below, dichains reconstituted using either native or wild-type recombinant L chains effectively blocked neuromuscular transmission in this assay. In contrast, dichain molecules reconstituted using the mutant L chain were completely inactive.

Example 19 describes the method used to demonstrate modified functional properties of reconstituted dichain toxins that incorporate recombinant L chains.

EXAMPLE 19

Assessment of the Effect of Reconstituted Toxins on Neuromuscular Transmission

Mouse phrenic nerve-hemidiaphragms were excised from Balb/C mice (20-25 g) and bathed in a closed circulatory superfusion system containing 10 ml of aerated Krebs-Ringer composed of (mM): NaCl, 118.0; KCl, 4.7; $MgSO_4$, 1.2; $CaCl_2$, 2.5; $NaHCO_3$, 23.8; $KH_2PO_4$, 1.2; glucose, 11.7, pH 7.4 (de Paiva et al, *J. Biol. Chem.* 268:20838 (1993)). Muscle twitch was evoked by supramaximal stimulation of the phrenic nerve and measured using a force-displacement transducer (Simpson *J. Pharmacol. Exp. Ther.* 212:16 (1980)).

Figure 8:
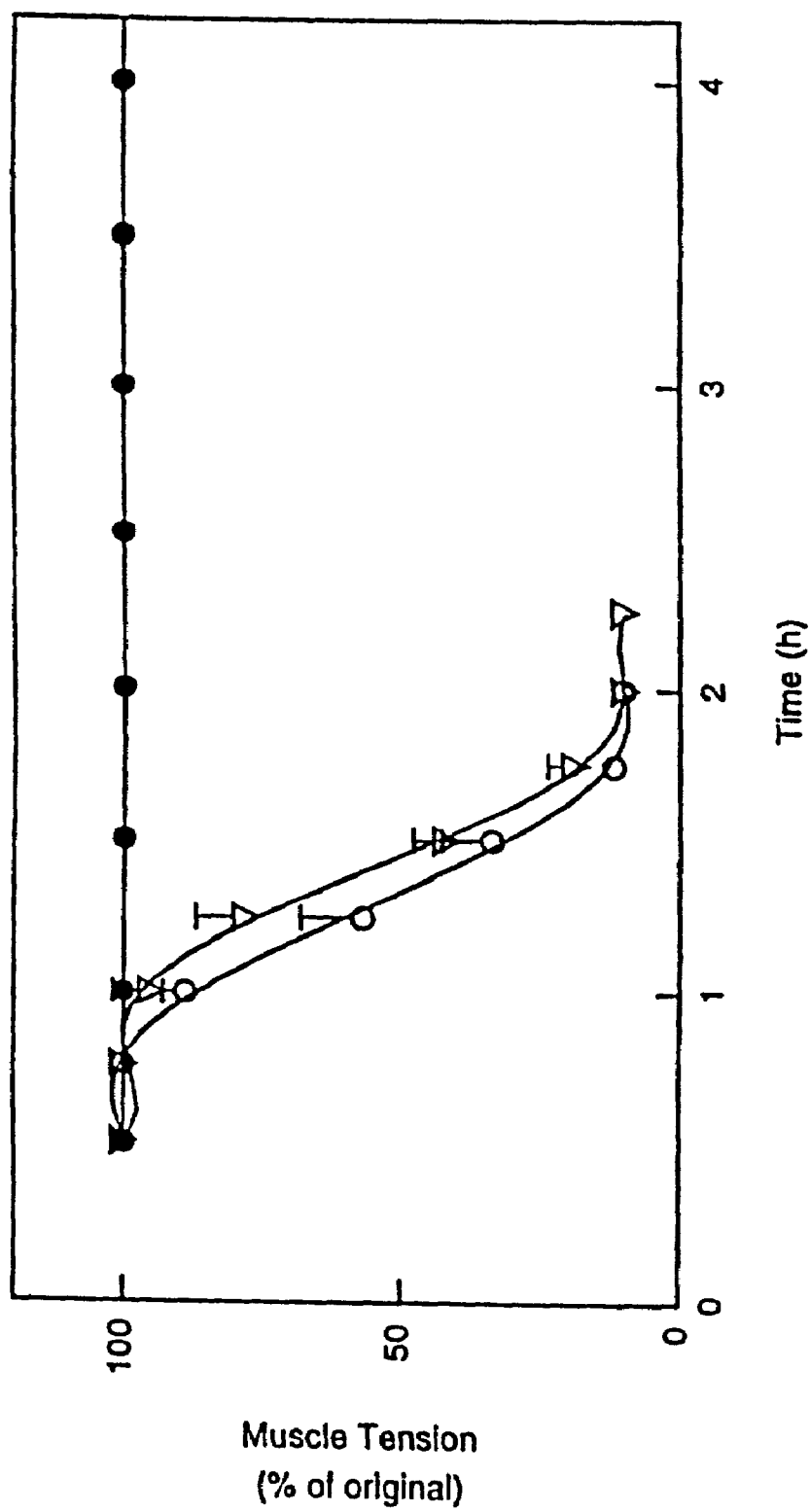
FIG. 8 is a line graph showing the effect of purified native and recombinant wild-type and mutant L chain on nerve-evoked neuromuscular transmission at motor end plates following reconstitution with the native H chain of BoNT/A. When applied to mouse phrenic nerve-hemidiaphrams, BoNT/A H chain reconstituted with recombinant L chain (1.6 nM; ○) blocked neuromuscular transmission with approximately the same efficacy as the native reconstituted L and H chains (2.0 nM; ∇). In contrast, even a larger amount of the dichain containing the Tyr$^{227}$ mutant form of the L chain (10 nM; ●) was incapable of affecting nerve-evoked muscle twitch. The concentrations of the reconstituted material were calculated following the quantification of the amount of the 150 kDa dichain material present by SDS-PAGE and densitometric scanning. The tissues were bathed in Krebs-Ringer medium aerated with 95% O$_2$ and 5% CO$_2$ maintained at 24° C. All points shown are the average of at least three separate experiments ±SD.

The results presented in FIG. 8 indicated that a dichain toxin reconstituted using the wild-type recombinant L chain blocked neuromuscular transmission nearly as effectively as a dichain that had been reconstituted using native L chains. The blockade of transmission by these reconstituted proteins was reversed upon the application of 0.3 mM 4-aminopyridine, a blocker of voltage-gated $K^+$ channels which temporarily restores nerve-evoked muscle tension at BoNT/A-poisoned synapses (Simpson *J. Pharmacol. Exp. Ther.* 245:867 (1988)). This finding proved that the inhibition by the recombinant L chain-containing sample resulted from a presynaptic blockade of transmitter release. Thus, the dichain toxin containing the wild-type recombinant L chain mimicked the activity of BoNT/A in this assay.

In contrast, the dichain material incorporating the Tyr[227] mutant L chain had no effect on nerve-evoked muscle twitch, even when tested at high concentrations. This absence of activity that characterized a dichain molecule that included a mutant L chain was fully consistent with the results of the SNAP-25 cleavage assay presented above. Significantly, results obtained in the nerve-hemidiaphragm assay extend the loss of activity to a clinically-relevant model at the toxin's site of action.

To further demonstrate the properties of dichain molecules that incorporate recombinant L chains, an experiment was carried out to test the abilities of these agents to cause botulism symptoms in mice.

Example 20 describes the methods used to prove that reconstituted dichains incorporating native or wild-type recombinant L chains, but not mutant L chains, had neurotoxic activity in vivo.

EXAMPLE 20

Assessment of the Mouse Lethality of Reconstituted Toxins and their Effect on Neuromuscular Transmission The ability of the reconstituted dichains to induce botulism was evaluated following intraperitoneal injection of laboratory mice. Results were expressed as the number of doses, lethal within 4 days, present per mg of protein ($LD_{50}$/mg) (Maisey et al., *Eur. J. Biochem.* 177:683 (1988)).

Toxicity of the dichain material containing the wild-type recombinant L chain ($6 \times 10^7$ $LD_{50}$/mg) was comparable to that of the dichain that had been reconstituted using native L chains ($7 \times 10^7$ $LD_{50}$/mg). Mice injected with the dichain that had been reconstituted using the Tyr[227] mutant showed no signs of botulism within four days. Therefore, by all in vitro and in vivo assays disclosed herein, the recombinant wild-type L chain expressed in E. coli is comparable to the potency of its native counterpart, while the mutated $Tyr^{227}$ L chain is devoid of activity.

To illustrate the general utility of recombinant BoNT/A-L chains prepared according to the method disclosed herein, we produced a second set of mutant fusion proteins that were devoid of proteolytic activity. More specifically, we demonstrated that mutagenesis of $Glu^{224}$ to Gln could eliminate enzymatic activity associated with the wild-type BoNT/A-L chain. Further, by employing a GST fusion protein in this demonstration, we confirmed the generality of our approach to producing recombinant BoNT/A-L chains.

Example 21 describes the methods used to construct a polynucleotide encoding a $Gln^{224}$ mutant BoNT/A-L chain fusion with the GST protein.

EXAMPLE 21

Preparation and Expression of BoNT/A-L Chain Fusions with GST

Polynucleotides encoding the BoNT/A wild-type, $Gln^{224}$ mutant and $Tyr^{227}$ mutant L chains were prepared exactly as described in Example 11 and Example 12. The amplification products were digested with Stu I and EcoR I, purified by agarose gel electrophoresis and ligated between the Sma I and EcoR I sites of the pGEX-2T expression vector (Pharmacia) to produce the plasmids pTAL-wild-type (GST), pTAL-$Gln^{224}$(GST) and pTAL-$Tyr^{227}$(GST). E. coli XL1-Blue transformants harboring the plasmids were isolated by standard methods.

Cultures of E. coli containing the expression constructs were induced to express the encoded fusion proteins exactly as described under Example 14. Following lysis of the cells, the GST fusion proteins were purified by glutathione affinity chromatography according to methods familiar to one having ordinary skill in the art. The GST fusion proteins were subsequently tested for proteolytic activity in an in vitro assay.

Example 22 describes the methods used to assess the proteolytic activity of the mutant BoNT/A-L chain GST fusion proteins.

EXAMPLE 22

Characterization of the BoNT/A-L Chain GST Fusions

The proteolytic activity of the isolated GST mutant L chain fusion protein toward a SNAP-25 substrate was assessed. After incubation of the purified mutant L chain fusion proteins and a recombinant GST-SNAP-25 substrate in 50 mM Tris-HCl (pH 8.0) for 2 hours or at 22° C. overnight, the products were analyzed by SDS-PAGE. Results of the analysis indicated that the mutant displayed no detectable proteolytic activity toward the SNAP-25 analog. In contrast, the wild-type recombinant L chain fusion protein proteolyzed the substrate. Thus, the GST mutant BoNT/A-L chain fusion protein, like the MBP mutant fusion protein, was enzymatically inactive. Further, the GST fusion protein having wild-type BoNT/A-L chain sequences was enzymatically active against the SNAP-25 substrate.

These results confirmed the importance of the amino acids making up the conserved HExxH motif of the BoNT/A-L chain, and demonstrated that fusion proteins other than MBP fusion proteins, can be used to produce recombinant proteins useful in the practice of the present invention. Whether formed as a GST fusion protein or as an MBP fusion protein, recombinant mutant BoNT/A L chains were devoid of the activities that characterized the native toxin, or reconstituted dichains that incorporated recombinant wild-type L chains.

The preceding Examples have illustrated how Clostridial L chains can be engineered for expression in recombinant form as active or attenuated molecules. These L chains have been reconstituted with native H chains to produce dichain molecules that possessed or lacked biological activities at the level of neuromuscular transmission. The following Example provides compelling evidence that dichain transporter molecules can be used as vehicles for the intracellular delivery of linked molecules.

A hybrid "tri-chain" molecule was used to make this exemplary demonstration. More specifically, a BoNT/A-L chain that was inactivated by virtue of a $Gln^{224}/Tyr^{227}$ double mutation was fused to an active portion of the TeTx-L chain. The resulting recombinant protein was reconstituted with the native BoNT/A-H chain to produce a "tri-chain." This tri-chain complex could bind and enter target neurons. Since the double mutant BoNT/A-L chain was devoid of enzymatic activity, neurotoxicity associated with the tri-chain was necessarily attributable to the presence of an active TeTx component. The results presented in the following Example confirmed that the transporter could be internalized by target cells and could deliver a linked molecule to the cytosol and the transported protein was active intracellularly. As disclosed below, a biochemical test ruled out any neurotoxic activity related to the BoNT/A-L chain.

Example 23 describes the method used to prove that transporters comprising inactive Clostridial L chains can be internalized into peripheral cholinergic nerve endings. Further, the results presented below indicated that such transporters were capable of delivering a linked molecule to the cytosol of target neurons in a state that retained biological activity intracellularly.

EXAMPLE 23

Clostridial Toxin Transporters as Vehicles for Biochemical Delivery

Figure 9:
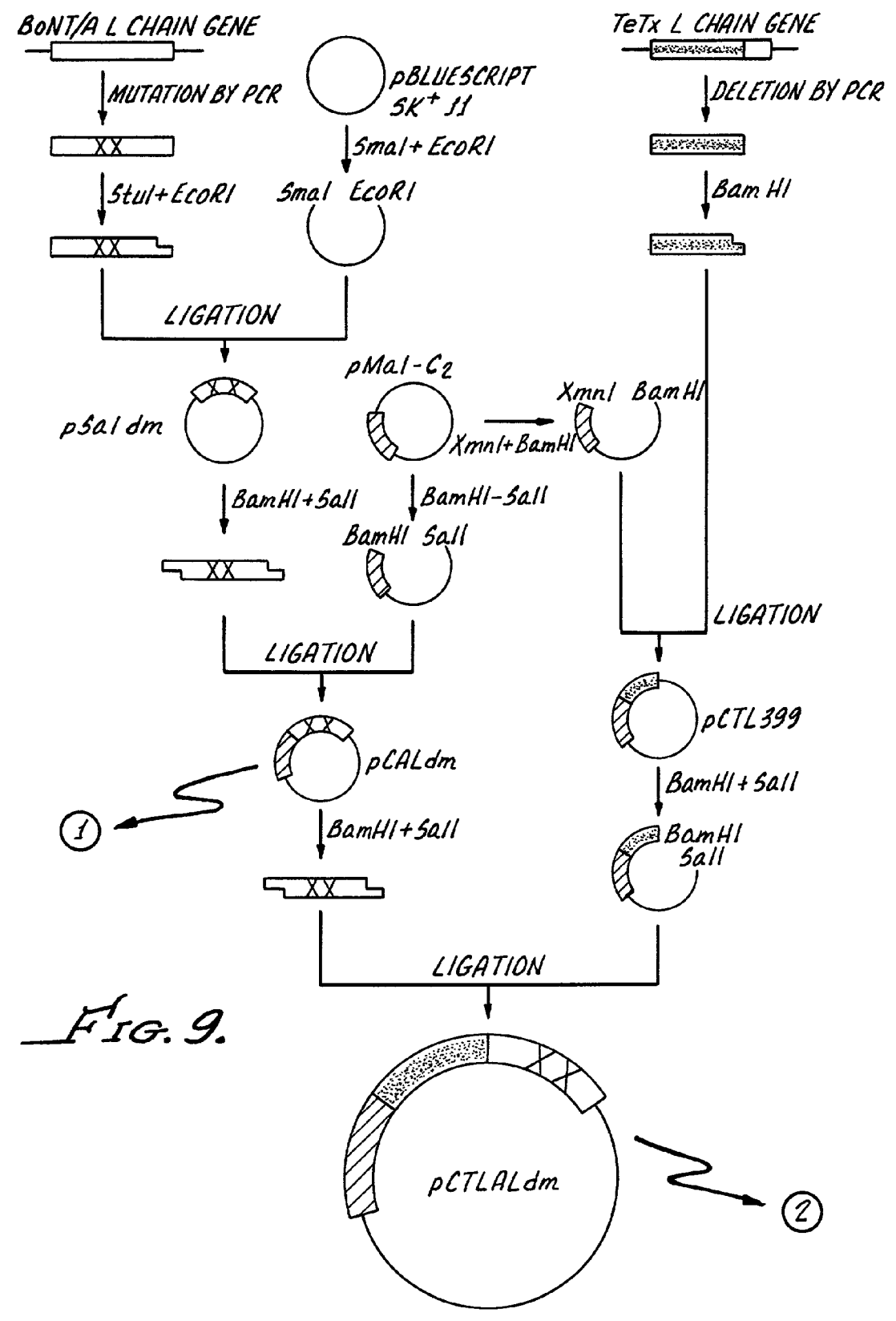

The L chain component of the tri-chain was produced according to the scheme presented in FIG. 9. A double mutation ($Glu^{224}$ to $Gln^{224}$ and $His^{227}$ to $Tyr^{227}$) was introduced into the BoNT/A-L chain by PCR mutagenesis. The primers and the methods utilized to generate the double mutant were the same as those used to produce the $Tyr^{227}$ mutant, except that the $Gln^{224}$ mutant was used as a template. The double mutant (dm) L chain was first cloned into pBluescript SK$^+$II, to form pSALdm, and thereafter cloned into pMAL-c2 to yield pCALdm. The pCALdm construct was employed to express the fusion protein having a maltose binding domain and a BoNT/A-L chain domain bearing a double mutation (MBP-BoNT/A dm). The pCALdm construct is labeled as "1" in FIG. 9. The TeTx-L chain was truncated by a PCR protocol using a polynucleotide harboring the cloned wild-type gene sequence as a template, together with primers having the sequences, 5'-ATTTCACCAATAACCAT-AAATAATTTTAG-3' (SEQ ID NO:12) and 5'-CGGGATCCTTCTGTATCATTGTAAAT-3' (SEQ ID NO:13). The amplification product encoded two additional amino acids at the N-terminus and was truncated at $Gly^{399}$. The last 58 residues, including $Cys^{439}$ which is normally responsible for disulfide bonding to H chain in native TeTx, was deleted. After cleavage with BamHI, the resulting DNA fragment was cloned into XmnI- and BamHI-digested pMAL-c2 to produce pCTL399. The MBP-truncated TeTx-L chain-BoNT/A-L chain dm gene fusion, pCTLALdm, was prepared by ligating the excised BoNT/A-L chain dm gene to BamHI- and SalI-digested pCTL399. The pCTLALdm construct, labeled as "2" in FIG. 9, was used to express the MBP-TeTx truncated L chain-BoNT/A-L chain dm fusion protein in E. coli.

Purified MBP-BoNT/A dm of L chain fusion protein encoded by the pCALdm construct failed to cleave a recombinant SNAP-25 substrate in an assay conducted according to the method of Example 16. Thus, the BoNT/A-L chain double mutant fusion protein was devoid of enzymatic activity, as expected. Following cleavage of the fusion protein with Factor $X_a$, purified BoNT/A-L chain double mutants were reconstituted with native BoNT/A-H chains to form dichain molecules. These dichains failed to block neuromuscular transmission at the mouse hemidiaphragm when tested by the method of Example 19. Thus, the dichain that incorporated the double mutant BoNT/A-L chain was devoid of biological activity in this in vitro assay, also as expected. Finally, the reconstituted dichain that incorporated the double mutant BoNT/A-L chain was non-toxic when injected into mice according to the method of Example 20. This was true even when the dichain that incorporated the double mutant BoNT/A-L chain was injected in an amount that was 200 fold greater than the $LD_{50}$ dose of native BoNT/A.

These results indicated that the $Gln^{224}/Tyr^{227}$ double mutation eliminated all toxic properties associated with the native BoNT/A molecule. Accordingly, any toxic activity associated with a transporter that incorporated the L chain double mutant must be attributed to a molecule linked to the inactive BoNT/A-L chain, since the transporter itself was devoid of toxic activity. Accordingly, the reconstituted dichain that incorporated the double mutant BoNT/A-L chain represented an ideal cholinergic transporter.

The purified TeTx truncated L chain-BoNT/A-L chain dm fusion protein, encoded by pCTLALdm, exhibited activities that were characteristic of TeTx, but not of BoNT/A. More specifically, the pCTLALdm-encoded fusion protein exhibited an ability to cleave synaptobrevin from neuronal membranes in a concentration dependent manner. This activity was not contributed by the BoNT/A L chain component of the complex, and highlighted the retention of endoprotease activity by the truncated TeTx-L chain component of the fusion. As expected, the pCTLALdm-encoded fusion protein lacked the ability to cleave a recombinant SNAP-25 substrate. This confirmed the successful elimination of enzymatic activity associated with the BoNT/A-L chain component of the fusion. After cleavage of the pCTLALdm-encoded fusion protein with Factor $X_a$, the released toxin hybrid was reconstituted with native BoNT/A-H chain to yield the tri-chain.

Most importantly, the tri-chain preparation produced symptoms characteristic of botulism both in vitro and in vivo. The tri-chain, at a 2 nM concentration, blocked nerve-evoked muscle twitch of mouse hemidiaphragm in 161 min at 24° C., and gave a mouse toxicity of $>10^7$ $LD_{50}$/mg. It should be noted that it was not, however, possible to provide exact quantitative data on the efficacy of this protein due to the presence of free MBP, uncleaved fusion protein and some native H chain in the reconstituted samples which preclude precise measurement of the amount of "tri-chain" present. Importantly, the block observed with the tri-chain in the hemidiaphragm assay was not reversed by 4-aminopyridine, a voltage-gated $K^+$ channel blocker which reverses BoNT/A but not TeTx-induced inhibition of neuromuscular transmission. Moreover, a contribution of the H chain (or any contaminating native BoNT/A) to the observed toxicity was ruled out by the observed absence of neuromuscular paralytic activity from larger quantities of the H chain that was used in the reconstitution and treated in an identical manner to the tri-chain material.

These results proved that the transporter targets motor nerve endings, becomes internalized, and can act as a vehicle to transport the linked segment of the TeTx-L chain to the cytosol. Additionally, the linked segment of the TeTx-L chain retained its biological activity following delivery into cholinergic nerves. The utility of this novel transporter as a drug delivery system for acetylcholine containing neurons has been clearly established.

In addition to the L chain modification strategy described in the preceding Example, native or recombinant botulinum toxin L chain proteins can be covalently linked to a chemical compound according to the method detailed in Example 8. The resulting transporter will then be available for administration as a sterile injection in a therapeutically effective dose.

The modified BoNT/A toxin transporters described above will have numerous clinical applications. For example, the BoNT/A-based transporters can be use to deliver therapeutically useful drugs to the peripheral motor terminal. Accordingly, these drugs delivered in this fashion will be useful in controlling limited numbers of muscle groups. Among the maladies that will be investigated as therapeutic targets are: tardive dyskinesia, spastic colitis, essential tremor, smooth muscle abnormalities, localized spasticity, painful muscle spasms localized to back or other muscle groups, temporal mandibular disorders, spasmodic dysphonia and tension headaches.

Example 24 describes how the chemically modified inactive BoNT/A toxin transporter described above can be used as a therapeutic agents for delivering chemical compounds to neurons that express toxin receptors.

EXAMPLE 24

Therapeutic Administration of Modified Toxins

Tardive Dyskinesia

A male patient, age 45, suffering from tardive dyskinesia resulting from the treatment with an antipsychotic drug, such as Thorazine or Haldo, is treated with therapeutically effective doses of an appropriate drug, as would be appreciated by one of ordinary skill in the art, attached to an inactive botulinum toxin transporter directly into the facial muscle muscles. After 1-3 days, the symptoms of tardive dyskinesia, i.e., orofacial dyskinesia, athetosis, dystonia, chorea, tics and facial grimacing, etc. are markedly reduced.

Example 25 further illustrates how the chemically modified inactive toxins described above can be used as therapeutic agents for delivering chemical compounds to neurons that express toxin receptors.

EXAMPLE 25

Therapeutic Administration of Modified Toxins

Essential Tremor

A male, age 45, suffering from essential tremor, which is manifested as a rhythmical oscillation of head or hand muscles and is provoked by maintenance of posture or movement, is treated by injection with therapeutically effective doses of a drug (see list in previous table in patent application)

attached to an inactive botulinum toxin transporter directly into the affected muscles. The muscles may be identified with the aide of electromyography (EMG). After one to two weeks, the symptoms are substantially alleviated; i.e., the patent's head or hand cases to oscillate.

Example 26 further illustrates how the chemically modified inactive BoNT/A toxin transporter described above can be used as therapeutic agents for delivering chemical compounds to neurons that express toxin receptors.

EXAMPLE 26

Therapeutic Administration of Modified Toxins

Smooth Muscle Abnormality

A female, age 30, with a constricted lower esophagus (disease called Achalasia) manifests symptoms which prevent food ingestion. Due to the lower esophagus contraction, food and fluid accumulate and eventually is regurgitated, preventing the patient from obtaining adequate nutrition. Therapeutically effective doses of a drug (see list in previous table in patent application) attached to an inactive botulinum toxin transporter is administered directly into the affected sphincter muscles. Usually the injections are administered in 2 to 4 quadrants with any endoscopic device or during surgery. In about 1-7 days, normal passage of solids and liquids into the stomach is achieved resulting in an elimination or reduction in regurgitation.

Example 27 further illustrates how the chemically modified inactive BoNT/A toxin transporter described above can be used as a therapeutic agent for delivering chemical compounds to neurons that express toxin receptors.

EXAMPLE 27

Therapeutic Administration of Modified Toxins

Spasmodic Dystonia (Overactive Vocal Chords)

A male, age 45, unable to speak clearly, due to spasm of the vocal chords, is treated by injection of the vocal chords by injection of therapeutically effective doses of an appropriate drug, as would be appreciated by one of ordinary skill in the art, attached to an inactive botulinum toxin transporter. After 1 to 7 days, the patient is able to speak clearly.

Thus, Example 27 shows another use for the inactive clostridial toxins of the present invention. In yet another use, the inactive toxins can be used in the treatment of botulism or tetanus. For such treatment, the inactive clostridial toxin is conjugated to an active ingredient for treatment of botulism or tetanus, such as Captopril or another zinc protease inhibitor.

A patient stricken with botulism or tetanus can be treated by administration of a therapeutically effective dose of the conjugate, such as through intramuscular injection. The proper therapeutically effective dose for any particular transporter/drug conjugate can be empirically determined using techniques readily known to those having ordinary skill in the art.

The inactive toxin alone can also be used as an immediate antidote to individuals exposed to botulinum toxin. For this purpose, administration should preferably be by injection of at least 1 mg of inactive toxin. Higher doses may be necessary in individuals exposed to higher levels of toxin. For this purpose, the inactive toxin alone can be used, without conjugation to another drug. It is believed that the use of this transporter will be more effective in treatment of botulinum toxin poisoning than prior art techniques, such as administration of botulinum toxin antisera.

In summary, we have gained further insight into the action of the TeTx and BoNT/A toxins by employing recombinant DNA techniques to produce L chain protein in useful quantities. Utilizing a PCR-based protocol, the genes encoding the L chains were amplified, subsequently cloned into expression vectors and expressed at high levels in *E. coli*. After purification from the cytosolic fraction using amylose affinity chromatography, fusion proteins representing wild-type sequences were found to proteolytically cleave a recombinant form of the substrate for BoNT/A, synaptosomal-associated protein of M, 25 kDa (SNAP-25). Moreover, once enzymatically cleaved from the maltose binding protein, the recombinant L chain proteins were shown to exhibit properties like those of the native proteins. Also, the expressed L chains were reconstituted with purified native H chains to form disulfide linked dichain proteins which inhibited nerve-evoked neuromuscular transmission in vitro and produced the symptoms of botulism in mice.

Most significantly, we also discovered that single amino acid substitutions in the sequence of the L chain proteins completely abrogated the proteolytic activity ordinarily associated with the wild-type proteins. This now allows the formation of dichain toxins that are attenuated by virtue of incorporating a proteolytically inactive L chain.

We also anticipate that single genes that incorporate appropriate site directed mutations can be produced for each of the neurotoxins so that attenuated toxins can be produced in bacteria. This approach will advantageously avoid the need to reconstitute dichain molecules from components. The resulting attenuated toxin can advantageously serve as a transporter for delivering covalently linked chemical compounds to neuronal cells that express toxin receptors.

We claim:

1. A composition comprising an active Clostridial neurotoxin joined to a neuropharmacological agent; wherein said active Clostridial neurotoxin comprises a tetanus toxin (TeTx) heavy chain and a TeTx light chain; possesses a mouse lethality of $3.3 \times 10^5$ LD50/mg or greater; has a binding specificity for, and is internalizable by, a target nerve cell; and has enzymatic activity for a target substrate selected from the group consisting of SNAP-25, VAMP and Cellubrevin.

2. The composition of claim 1 wherein said neuropharmacological agent is an intracellular acting drug.

3. The composition of claim 1 wherein said neuropharmacological agent is selected from the group consisting of a protein synthesis toxin, an inhibitor of neurotransmitter release, neuronal calcium channel blocker, a ribozyme and an oligonucleotide.

4. A pharmaceutical composition for treatment of a neuromuscular dysfunction in a mammal, comprising an active Clostridial neurotoxin comprising a TeTx heavy chain and a TeTx light chain, joined to a neuropharmacological agent; and a pharmaceutically acceptable excipient; wherein the active neurotoxin possesses mouse lethality of $3.3 \times 10^5$ LD$_{50}$/mg or greater and has binding specificity for and is internalizable by a target nerve cell, and has enzymatic activity for a target substrate selected from the group consisting of SNAP-25, VAMP and Cellubrevin.

5. The pharmaceutical composition of claim 4 wherein the neuromuscular dysfunction is characterized by uncontrollable muscle spasms.

6. The composition of either of claims 1 or 4 wherein the neuropharmacological agent is an inhibitor of neurotransmitter release.

7. The composition of either of claims 1 or 4 wherein the neuropharmacological agent is an active ingredient for treatment of botulism or tetanus.

8. The composition of either of claims 1 or 4 wherein the neuropharmacological agent is selected from the group consisting of a GABA agonist, a neuronal calcium channel agonist, an adenosine agonist, a glutamate antagonist, an inhibitor of neurotransmitter release, a protein synthesis toxin, a zinc-dependent protease inhibitor, a neuronal growth factor, an antiviral agent, a nicotinic antagonist, a neuronal calcium channel blocker, an acetylcholine esterase inhibitor, a potassium channel activator, a vasamicol inhibitor, a ribozyme and a transcribable gene.

* * * * *

UNITED STATES PATENT AND TRADEMARK OFFICE
CERTIFICATE OF CORRECTION

PATENT NO. : 7,628,992 B1  Page 1 of 1
APPLICATION NO. : 09/676053
DATED : December 8, 2009
INVENTOR(S) : Dolly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1513 days.

Signed and Sealed this

Second Day of November, 2010

David J. Kappos
*Director of the United States Patent and Trademark Office*

SEQUENCE LISTING

<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<221> NAME/KEY: primer_bind
<222> LOCATION: (1)...(33)
<223> OTHER INFORMATION: PCR primer for amplification of C. tetani
      neurotoxin L chain

<400> SEQUENCE: 1
gagatggtcg acatgccaat aaccataaat aat                                    33

<210> SEQ ID NO 2
<211> LENGTH: 32
<212> TYPE: DNA
<213> ORGANISM: Artificial Sequence
<220> FEATURE:
<221> NAME/KEY: primer_bind
<222> LOCATION: (1)...(32)
<223> OTHER INFORMATION: PCR primer for amplification of C. tetani
      neurotoxin L chain

<400> SEQUENCE: 2
acgcgaagct tttatcatgc agttctatta ta                                     32

<210> SEQ ID NO 3
<211> LENGTH: 30
<212> TYPE: DNA
<213> ORGANISM: Artificial Sequence
<220> FEATURE:
<221> NAME/KEY: primer_bind
<222> LOCATION: (1)...(30)
<223> OTHER INFORMATION: PCR primer for site-directed mutagenesis and
      amplification of C. tetani neurotoxin L chain

<400> SEQUENCE: 3
tagtacatgt ataagtgcgt gcattaatag                                        30

<210> SEQ ID NO 4
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: PCR primer for site-directed mutagenesis and
      amplification of C. tetani neurotoxin L chain

<400> SEQUENCE: 4
ttatacatgt actacatggt                                                   20

<210> SEQ ID NO 5
<211> LENGTH: 23
<212> TYPE: DNA
<213> ORGANISM: Artificial Sequence
<220> FEATURE:
<221> NAME/KEY: primer_bind
<222> LOCATION: (1)...(23)
<223> OTHER INFORMATION: PCR primer for amplification of C. botulinum
      neurotoxin L chain

<400> SEQUENCE: 5
aaaggccttt tgttaataaa caa                                               23

<210> SEQ ID NO 6
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: PCR primer for amplification of C. botulinum
      neurotoxin L chain

<400> SEQUENCE: 6
ggaattctta cttattgtat ccttta                                            26

```
<210> SEQ ID NO 7
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: PCR primer for site-directed mutagenesis and
      amplification of C. botulinum neurotoxin L chain

<400> SEQUENCE: 7
gcacatcaac ttatacat                                                18

<210> SEQ ID NO 8
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: PCR primer for site-directed mutagenesis and
      amplification of C. botulinum neurotoxin L chain

<400> SEQUENCE: 8
atgtataagt tgatgtgc                                                18

<210> SEQ ID NO 9
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: PCR primer for site-directed mutagenesis and
      amplification of C. botulinum neurotoxin L chain

<400> SEQUENCE: 9
aacttatata tgctggac                                                18

<210> SEQ ID NO 10
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: PCR primer for site-directed mutagenesis and
      amplification of C. botulinum neurotoxin L chain

<400> SEQUENCE: 10
gtccagcata tataagtt                                                18

<210> SEQ ID NO 11
<211> LENGTH: 13
<212> TYPE: PRT
<213> ORGANISM: Artificial Sequence
<220> FEATURE:
<221> NAME/KEY: SITE
<222> LOCATION: (1)...(13)
<223> OTHER INFORMATION: Portion of predicted amino acid sequence of
      human SNAP-25

<400> SEQUENCE: 11

Cys Ala Asn Gln Arg Ala Thr Lys Met Leu Gly Ser Gly
 1               5                  10

<210> SEQ ID NO 12
```

```
<211> LENGTH: 29
<212> TYPE: DNA
<213> ORGANISM: Artificial Sequence
<220> FEATURE:
<221> NAME/KEY: primer_bind
<222> LOCATION: (1)...(29)
<223> OTHER INFORMATION: PCR primer for   amplification of C. tetani
      neurotoxin L chain

<400> SEQUENCE: 12
atttcaccaa taaccataaa taattttag                                            29

<210> SEQ ID NO 13
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: PCR primer for   amplification of C. tetani
      neurotoxin L chain

<400> SEQUENCE: 13
cgggatcctt ctgtatcatt gtaaat                                               26

<210> SEQ ID NO 14
<211> LENGTH: 63
<212> TYPE: DNA
<213> ORGANISM: Artificial Sequence
<220> FEATURE:
<221> NAME/KEY: misc_feature
<222> LOCATION: (1)...(63)
<223> OTHER INFORMATION: Polylinker region

<400> SEQUENCE: 14
atcgagggaa ggatttcaga attcggatcc tctagagtcg acatgccaat aaccataaag          60
ctt                                                                       63

<210> SEQ ID NO 15
<211> LENGTH: 11
<212> TYPE: PRT
<213> ORGANISM: Artificial Sequence
<220> FEATURE:
<221> NAME/KEY: SITE
<222> LOCATION: (1)...(11)
<223> OTHER INFORMATION: Wild-type region of C. tetani light chain

<400> SEQUENCE: 15

Leu Leu Met His Glu Leu Ile His Val Leu His
 1               5                  10

<210> SEQ ID NO 16
<211> LENGTH: 11
<212> TYPE: PRT
<213> ORGANISM: Artificial Sequence
<220> FEATURE:
<221> NAME/KEY: VARIANT
<222> LOCATION: (5)...(5)
<223> OTHER INFORMATION: Ala 234 mutant region of C. tetani light chain

<400> SEQUENCE: 16

Leu Leu Met His Ala Leu Ile His Val Leu His
 1               5                  10

<210> SEQ ID NO 17
<211> LENGTH: 13
<212> TYPE: PRT
<213> ORGANISM: Artificial Sequence
```

```
-continued

<220> FEATURE:
<221> NAME/KEY: SITE
<222> LOCATION: (1)...(13)
<223> OTHER INFORMATION: Polylinker region

<400> SEQUENCE: 17

Ile Glu Gly Arg Ile Ser Glu Phe Gly Ser Pro Pro Phe
 1               5                  10

<210> SEQ ID NO 18
<211> LENGTH: 39
<212> TYPE: DNA
<213> ORGANISM: Artificial Sequence
<220> FEATURE:
<221> NAME/KEY: misc_feature
<222> LOCATION: (1)...(39)
<223> OTHER INFORMATION: Polylinker region

<400> SEQUENCE: 18
atcgagggaa ggatttcaga attcggatcc cccccttt                           39

<210> SEQ ID NO 19
<211> LENGTH: 19
<212> TYPE: PRT
<213> ORGANISM: Artificial Sequence
<220> FEATURE:
<221> NAME/KEY: SITE
<222> LOCATION: (1)...(19)
<223> OTHER INFORMATION: Polylinker region

<400> SEQUENCE: 19

Ile Glu Gly Arg Ile Ser Glu Phe Gly Ser Ser Arg Val Asp Met Pro
 1               5                  10                  15

Ile Thr Ile
```